United States Patent
Kowalik et al.

(10) Patent No.: US 10,260,066 B2
(45) Date of Patent: *Apr. 16, 2019

(54) THERAPEUTIC ALTERATION OF TRANSPLANTABLE TISSUES THROUGH IN SITU OR EX VIVO EXPOSURE TO RNA INTERFERENCE MOLECULES

(71) Applicant: University of Massachusetts, Boston, MA (US)

(72) Inventors: Timothy F. Kowalik, Princeton, NJ (US); Marc E. Uknis, Chadds Ford, PA (US)

(73) Assignee: University of Massachusetts, Boston, MA (US)

(*) Notice: Subject to any disclaimer, the term of this patent is extended or adjusted under 35 U.S.C. 154(b) by 59 days.

This patent is subject to a terminal disclaimer.

(21) Appl. No.: 14/840,187

(22) Filed: Aug. 31, 2015

(65) Prior Publication Data

US 2016/0024507 A1  Jan. 28, 2016

Related U.S. Application Data

(63) Continuation of application No. 14/591,073, filed on Jan. 7, 2015, now Pat. No. 9,150,861, which is a continuation of application No. 13/738,353, filed on Jan. 10, 2013, now Pat. No. 8,940,709, which is a continuation of application No. 11/179,792, filed on Jul. 11, 2005, now Pat. No. 8,361,976.

(60) Provisional application No. 60/586,530, filed on Jul. 9, 2004.

(51) Int. Cl.
| | |
|---|---|
| *C12N 15/113* | (2010.01) |
| *C12N 15/11* | (2006.01) |
| *A61K 48/00* | (2006.01) |
| *A01N 1/02* | (2006.01) |

(52) U.S. Cl.
CPC .......... *C12N 15/113* (2013.01); *A01N 1/0226* (2013.01); *A61K 48/005* (2013.01); *C12N 15/111* (2013.01); *C12N 15/1135* (2013.01); *C12N 15/1136* (2013.01); *C12N 2310/14* (2013.01); *C12N 2320/30* (2013.01)

(58) Field of Classification Search
None
See application file for complete search history.

(56) References Cited

U.S. PATENT DOCUMENTS

| 5,586,438 | A | 12/1996 | Fahy |
|---|---|---|---|
| 5,859,226 | A | 1/1999 | Hunt et al. |
| 6,365,577 | B1 | 4/2002 | Iversen |
| 8,263,756 | B2 | 9/2012 | Takahara et al. |
| 2002/0086356 | A1 | 7/2002 | Tuschl et al. |
| 2003/0109435 | A1 | 6/2003 | Prenner et al. |
| 2003/0125273 | A1 | 7/2003 | Bennett et al. |
| 2003/0143732 | A1 | 7/2003 | Fosnaugh et al. |
| 2003/0144232 | A1 | 7/2003 | Agami et al. |
| 2003/0144239 | A1 | 7/2003 | Agami et al. |
| 2003/0148519 | A1 | 8/2003 | Engelke et al. |
| 2003/0157030 | A1 | 8/2003 | Davis et al. |
| 2003/0157514 | A1 | 8/2003 | Finger et al. |
| 2003/0199002 | A1 | 10/2003 | Hekimi et al. |
| 2004/0019001 | A1* | 1/2004 | McSwiggen ..... A61K 47/48023 514/44 A |
| 2004/0038921 | A1 | 2/2004 | Kreutzer et al. |
| 2004/0053876 | A1 | 3/2004 | Turner et al. |
| 2004/0091936 | A1 | 5/2004 | West |
| 2004/0127446 | A1 | 7/2004 | Blatt et al. |
| 2004/0209801 | A1 | 10/2004 | Brand et al. |
| 2005/0014166 | A1 | 1/2005 | Trono et al. |
| 2005/0032733 | A1 | 2/2005 | McSwiggen et al. |
| 2005/0227940 | A1 | 10/2005 | Rossi et al. |

(Continued)

FOREIGN PATENT DOCUMENTS

| WO | WO 03/017817 | 3/2003 |
|---|---|---|
| WO | WO 03/020024 | 3/2003 |

(Continued)

OTHER PUBLICATIONS

Lemasters, et al. (1997) Reperfusion Injury After Liver Preservation for Transplantation. Annu. Rev. Pharmacol. Toxicol., V.37:327-38. (Year: 1997).*
Bradley et al., "Successful Incorporation of Short-Interfering RNA Into Islet Cells by in Situ Perfusion", Transplantation Proceedings, 2005, 37, 233-236.
Bradley et al., "Gene Silencing in the Endocrine Pancreas Mediated by Short-Interfering RNA", Pancreas, 2005, 31(4), 373-379.
Brown et al., "Three-dimensional Structure of the Human Class II Histocompatibility Antigen HLA-DR1", Nature, 1993, 364, 33-39.
Bucchini et al., "Pancreatic Expression of Human Insulin Gene in Transgenic Mice", Proc. Natl. Acad. Sci., 1986, 83, 2511-2515.
Contreras et al., "A Novel Approach to Xenotransplantation Combining Surface Engineering and Genetic Modification of Isolated Adult Porcine Islets", Surgery, 2004, 136, 537-547.

(Continued)

*Primary Examiner* — Jennifer Pitrak McDonald
(74) *Attorney, Agent, or Firm* — BakerHostetler

(57) ABSTRACT

The present invention, at least in part, relates to the discovery of efficacious delivery of an RNAi agent (in preferred aspects of the invention, an siRNA) to a transplantable tissue. Organ rejection, transplantation-mediated transmission of viral infection, and triggering of apoptosis in transplanted tissues can each be minimized by the methods and compositions of the instant invention. The RNAi agent(s) of the instant invention can be delivered as "naked" molecules, or using liposomal and other modes of delivery, to transplantable tissues. Such delivery can occur via perfusion of the RNAi agent in solution through the vasculature of a whole or partial organ; or tissues including transplantable cells and cell lines may be bathed, injected or otherwise treated with RNAi agents. Preferred transplantable tissues include, for example, pancreas, liver, kidney, heart, lung, and all cells and cell lines derived from such tissues (e.g., pancreatic islet cells that may, e.g., be transplanted as a treated population).

9 Claims, 5 Drawing Sheets

Specification includes a Sequence Listing.

(56) References Cited

U.S. PATENT DOCUMENTS

| | | |
|---|---|---|
| 2005/0287129 A1 | 12/2005 | Cicciarelli et al. |
| 2006/0165665 A1 | 7/2006 | Min et al. |
| 2008/0287382 A1 | 11/2008 | Feinstein et al. |
| 2010/0028848 A1 | 2/2010 | Parker et al. |

FOREIGN PATENT DOCUMENTS

| | | |
|---|---|---|
| WO | WO 03/029277 | 4/2003 |
| WO | WO 03/056012 | 7/2003 |
| WO | WO 03/070905 | 8/2003 |
| WO | WO 03/089613 | 10/2003 |
| WO | WO 03/099227 | 12/2003 |
| WO | WO 03/099859 | 12/2003 |
| WO | WO 03/104456 | 12/2003 |
| WO | WO 03/104488 | 12/2003 |
| WO | WO 2004/001060 | 12/2003 |
| WO | WO 2004/009794 | 1/2004 |
| WO | WO 2004/009796 | 1/2004 |
| WO | WO 2004/011647 | 2/2004 |
| WO | WO 2004/013310 | 2/2004 |
| WO | WO 2004/014933 | 2/2004 |
| WO | WO 2004/016731 | 2/2004 |
| WO | WO 2004/016735 | 2/2004 |
| WO | WO 2004/027063 | 4/2004 |
| WO | WO 2004/002512 | 8/2004 |

OTHER PUBLICATIONS

Contreras et al., "Caspase-8 and Caspase-3 Small Interfering RNA Decreases Ischemia/Reperfusion Injury to the Liver in Mice", Surgery, 2004, 136, 390-400.

Docherty et al., "Nutrient Regulation of Insulin Gene Expression", FASEB J., 1994, 8, 20-27.

Elbashir et al, "Duplexes 21-Nucleotide RNAs Mediate RNA Interference in Cultured Mammalian Cells", Nature, 2001, 411, 494-498.

Fujino et al., "Silencing of p53 RNA Through Transarterial Delivery Ameliorates Renal Tubular Injury and Downregulates GSK-3Beta Expression After Ischemia-Reperfusion Injury", Am J. Physiol. Renal Physiol., 2013, 305, F1617-F1627.

Grishok et al., "Genes and Mechanisms Related to RNA Interference Regulate Expression of the Small Temporal RNAs That Control C. Elegans Developmental Timing", Cell, 2001, 106, 23-34.

Hannon, "RNA Interference", Nature, 2002, 418, 244-251.

Huang et al., "Functional Silencing of Hepatic Microsomal Glucose-6-Phosphatase Gene Expression in Vivo by Adenovirus-Mediated Delivery of Short Hairpin RNA", FEBS Letters, 2004, 558, 69-73.

Hutvagner et al, "A MicroRNA in a Multiple-Turnover RNAi Enzyme Complex", Science, 2002, 297, 2056-2060.

Hutvagner et al, "RNAi: Nature Abhors a Double-Strand", Current Opinion in Genetics & Development, 2002, 12, 225-232.

Jacque et al, "Modulation of HIV-1 Replication by RNA Interference", Nature, 2002, 418, 435-438.

Katayama et al., "RNA Interfering Approach for Clarifying the PPAPg Pathway Using Lentiviral Vector Expressing Short Hairpin RNA", FEBS Letters, 2004, 560, 178-182.

Lagos-Quintana et al., "Identification of Novel Genes Coding for Small Expressed RNAs", Science, 2001, 294, 853-858.

Lakso et al., "Targeted Oncogene Activation by Site-Specific Recombination in Transgenic Mice", Proc. Nat. Acad. Sci., 1992, 89, 6232-6236.

Lau et al., "An Abundant Class of Tiny RNAs with Probable Regulatory Roles in Caenorhabditis Elegans", Science, 2001, 294, 858-862.

Lee et al., "Myosin Light Chain-2 Luciferase Transgenic Mice Reveal Distinct Regulatory Programs for Cardiac and Skeletal Muscle-Specific Expression of a Single Contractile Protein Gene", Journal of Biological Chemistry, 1992, 267(22), 15875-15885.

Lee et al., "Functional Analysis of the Endothelin-1 Gene Promoter", Journal of Biological Chemistry, 1990, 265(18), 10446-10450.

Li et al., "Induction and Suppression of RNA Silencing by an Animal Virus", Science, 2002, 296, 1319-1321.

Llave et al., "Cleavage of Scarecrow-Like mRNA Targets Directed by a Class of Arabidopsis miRNA", Science, 2002, 297, 2053-2056.

McCaffrey et al., "RNA Interference in Adult Mice", Nature, 2002, 418, 38-39.

McManus et al., "Gene Silencing in Mammals by Small Interfering RNAS", Nature Reviews/Genetics, 2002, 3, 737-747.

Mills, "Changing Colors in Mice: An Inducible System That Delivers", Genes & Development, 2001, 15, 1461-1467.

Molitoris et al., "siRNA Targeted to p53 Attenuates Ischemic and Cisplatin-Induced Acute Kidney Injury", J. Am. Soc. Nephrol, 2009, 20, 1754-1764.

Morello et al., "Studies on the Expression of an H-2K/Human Growth Hormone Fusion Gene in Giant Transgenic Mice," EMBO Journal, 1983, 5(8), 1877-1883.

Ocker, et al., "Bcl-2 Specific siRNA Molecules Inhibit Growth of Pancreatic Cancer in Vitro and in Vivo", European Journal of Cancer, 2002, 38(Supp 7), S142-S143.

Ogilvy et al., "Constitutive Bcl-2 Expression Throughout the Hematopoietic Compartment Effects Multiple Lineages and Enhances Progenitor Cell Survival", PNAS, 1999, 96(26), 14943-14948.

Pinkert et al., "An Albumin Enhancer Located 10 kb Upstream Functions Along with its Promoter to Direct Efficient, Liver-Specific Expression in Transgenic Mice", Genes & Development, 1987, 1, 268-276.

Rhoades et al., "Prediction of Plant MicroRNA Targets", Cell, 2002, 110, 513-520.

Roitt et al., "Immunology", Gower Medical Publishing ($2^{nd}$ Ed), London (1989).

Samuel, "Antiviral Actions of Interferons", Clinical Microbiology Reviews, 2001, 14(4), 778-809.

Schwarz et al., "Evidence of siRNAs Function as Guides, Not Primers, in the Drosophila and Human RNAi Pathways", Molecular Cell, 2002, 10, 537-548.

Stern et al., "Crystal Structure of the Human Class II MHC Protein HLA-DR1 Complexed with an Influenza Virus Peptide", Nature, 1994, 368, 215-221.

Udaka et al., "A Ubiquitous Protein is the Source of Naturally Occurring Peptides that are Recognized by a CD8+ T-Cell Clone", Proc. Natl. Acad. Sci., 1993, 90, 11272-11276.

Voinnet, "RNA Silencing as a Plant Immune System Against Viruses", Trends in Genetics, 2001, 17(8), 449-459.

Waterhouse et al., "Gene Silencing as an Adaptive Defense Against Viruses", Nature, 2001, 411, 834-842.

Zamore et al., "RNAi: Double-Stranded RNA Directs the ATP-Dependent Cleavage of mRNA at 21 to 23 Nucleotide Intervals", Cell, 2000, 101, 25-33.

Zheng et al., "Gene Silencing of Complement C5a Receptor Using siRNA for Preventing Ischemia/Reperfusion Injury", American Journal of Pathology, 2008, 173(4), 973-980.

Zheng et al., "Protection of Renal Ischemia Injury Using Combination Gene Silencing of Complement 3 and Caspase 3 Genes", Transplantation, 2006, 82(12), 1781-1786.

* cited by examiner

SEQUENCE LISTING

```
<160> NUMBER OF SEQ ID NOS: 11

<210> SEQ ID NO 1
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
aacgacagcc cagaagagga a                                              21

<210> SEQ ID NO 2
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
cagaaauguc cugcaauuu                                                 19

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
```

```
<220> FEATURE:
<223> OTHER INFORMATION: Description of Combined DNA/RNA Molecule:
      Synthetic oligonucleotide

<400> SEQUENCE: 3
gugaagucaa caugccugct t                                              21

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 4
uauggagcug cagaggaugt t                                              21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 5
gaagacauca uccggaauat t                                              21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 6
uggauuaucc ugagaugggt t                                              21

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 7
cuaccagaaa gguauaccut t                                              21

<210> SEQ ID NO 8
<211> LENGTH: 21
<212> TYPE: RNA
<213> ORGANISM: Artificial Sequence
<220> FEATURE:
<223> OTHER INFORMATION: Description of Artificial Sequence: Synthetic
```

-continued

```
      oligonucleotide

<400> SEQUENCE: 8
gugaaccagg augggucacc a                                          21

<210> SEQ ID NO 9
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
gggcaagagu gcgcugacca uc                                         22

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 10
cugcucaaca aguggguuut t                                          21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 11
guuuucagag ccguguuuut t                                          21
```

THERAPEUTIC ALTERATION OF TRANSPLANTABLE TISSUES THROUGH IN SITU OR EX VIVO EXPOSURE TO RNA INTERFERENCE MOLECULES

RELATED APPLICATIONS

This application is a continuation of U.S. Utility application Ser. No. 14/591,073, filed Jan. 7, 2015 (now allowed), which is a continuation of Ser. No. 13/738,353, filed Jan. 10, 2013 U.S. Pat. No. 8,940,709, which in turn is a continuation of U.S. Utility application Ser. No. 11/179,792, entitled "Therapeutic Alteration of Transplantable Tissues Through In Situ or Ex Vivo Exposure to RNA Interference Molecules" filed Jul. 11, 2005, now U.S. Pat. No. 8,361,976 and which in turn claims the benefit of U.S. Provisional Patent Application Ser. No. 60/586,530, filed Jul. 9, 2004, entitled "Therapeutic Alteration of Transplantable Tissues Through In Situ or Ex Vivo Exposure to RNA Interference Molecules." The entire contents of the referenced applications are incorporated herein by reference.

SEQUENCE LISTING

The instant application contains a Sequence Listing which has been filed electronically in ASCII format and is hereby incorporated by reference in its entirety. Said ASCII copy, created on Aug. 28, 2015, is named Sequence_ Listing_CRF_101739-000004 and is 3,676 bytes in size.

BACKGROUND OF THE INVENTION

Organ rejection is the process whereby a patient's own immune system recognizes the cell surface markers (antigens) within a transplanted organ as foreign (Joosten et al., 2003, *Transpl Int*, 2003 16, 137-45) Immunologic recognition of foreign cell surface antigens leads to destruction of the foreign tissue: in the case of transplanted organs, the chronic rejection process destroys the functionality of the transplant. Class I or class II "major histocompatibility (MHC)" antigen on the surface of the transplanted organ's cells are processed and presented to the host immune system. Classic initiation of rejection occurs when class II molecules are expressed and activate T-helper ($CD4^+$) lymphocytes. Cytokines thus released by activated $CD4^+$ cells, lead to margination and recognition of foreign class I molecules by cytotoxic T lymphocytes ($CD8^+$, CTL) (Buckley, R. H. *J Allergy Clin Immunol*, 2003.111, S733-44). This process has been controlled with current pharmacotherapy to the point of reducing acute rejection episodes to around 10% within 1 year after transplantation (Ciancio, G., et al., *Transplantation*, 2004 77, 244-51). However, most antirejection medications are toxic to the patient and given long-term, may induce organ toxicity (Baran, D. A., et al. *Am J Cardiovasc Drugs*, 2004 4, 21-9) and malignancy (Ganschow, R., et al., *J Pediatr Gastroenterol Nutr*, 2004 38, 198-203) in some patients. Tolerance in transplantation is the process by which a transplant is performed and maintained without the need for exogenous drugs to prevent rejection.

Infection also presents a significant obstacle to successful transplantation. Despite the use of novel antiviral and antibiotic therapeutics, opportunistic infections continue to add to the morbidity and mortality associated with transplantation. Herpesviruses, as an example, account for serious disease in as many as 50% of transplant recipients (Aiello, F. B., et al., *Mod Pathol*, 2004.17, 189-96) and this leads to poor outcomes for many of the infected patients. These viruses incorporate their genome into the cells of a transplanted graft and as such, the transplanted organ serves as a reservoir for reactivation and infection in the transplant recipient. Hepatitis C virus leads to cirrhosis and is the most common cause of liver failure amongst patients awaiting liver transplantation. Recurrence of the Hepatitis C in the transplanted liver occurs 100% of the time and leads to graft failure (Neumann, U. P., et al., *Transplantation*, 2004 77, 226-31) and death in nearly 10% of these patients. CMV and Hepatitis C are just two examples of viruses that cause poor outcomes in transplant patients.

Successful transplantation is also limited by ischemic injury (lack of oxygen) to the transplanted organ as it is removed from a donor. Islet cell transplantation, as an example, is dependant upon high yield of viable islets separated from a cadaver pancreas. Islet viability is diminished as a result of apoptosis (programmed cell death) initiated by insults such as ischemia induced in the organ procurement process. There are current strategies that are being employed in genetically altering islets to prevent such ischemic loss (Fenjves, E. S., et al., *Transplantation*, 2004 77, 13-8). Islets from Balb/c mice have been transduced with a replication-deficient adenovirus expressing wild-type Survivin (pAd-Survivin; G. P. Basadonna, *PhD. Thesis of Charlotte Ariyan, MD*. Yale Univ. 2003). Survivin, first described in some human cancers, is a gene related to bcl-2 or the baculovirus IAP (inhibitor of apoptosis) gene (Ambrosini, G., C., et al. *Nat Med*, 1997.3, 917-21), but functions independently (Adida, C, et al., Lancet, 1998 351, 882-3). Recombinant expression of Survivin counteracts apoptosis in B lymphocyte precursors (Ambrosini, G., C., et al. *Nat Med*, 1997 3, 917-21). While not normally expressed in adult cells, Survivin expression can and does occur. Enhanced expression of Survivin has been consistently associated with inhibition of apoptosis, in vitro (Kobayashi, K., et al., *Proc Natl Acad Sci USA*, 1999 96, 1457-62; Tamm, L, et al., *Cancer Res*, 1998 58, 5315-20; Mahotka, C, et al. *Cancer Res*, 1999 59, 6097-102; Suzuki, A., et al., *Oncogene*, 2000 19, 1346-53; Islam, A., et al., *Med Pediatr Oncol*, 2000 35, 550-3) and in vivo (Grossman, D., et al., *J Clin Invest*, 2001 108, 991-9).

In spite of continuing advances in transplantation technology, serious morbidity and mortality are still associated with transplantation. Genetic alteration in many ways can be harnessed to improve transplantation outcomes; however, genetic alteration of tissue has thus far been most effectively performed through use of viral intermediaries (such as adenoviral transfection). Such use of viral vectors continues to present a serious danger to transplant patients; and a safer, efficacious method of preventing rejection of transplanted tissues is highly desirable.

SUMMARY OF THE INVENTION

The present invention is based, at least in part, on the discovery of efficacious delivery of an RNAi agent (in preferred aspects of the invention, an siRNA) to a transplantable tissue. Organ rejection, transplantation-mediated transmission of viral infection, and triggering of apoptosis in transplanted tissues may each be minimized by the methods and compositions of the instant invention. The RNAi agent(s) of the instant invention may be delivered as "naked" molecules, or using liposomal and other modes of delivery, to transplantable tissues. Such delivery may occur via perfusion of the RNAi agent in solution through the vasculature of a whole or partial organ, or tissues including transplantable cells and cell lines may be bathed, injected or otherwise treated with RNAi agents. Preferred transplantable tissues include, for example, pancreas, liver, kidney, heart, lung, and all cells and cell lines derived from such tissues (e.g., pancreatic islet cells that may, e.g., be transplanted as a treated population).

The present invention therefore provides methods for countering potential negative transplantation outcomes, including:

methods for treating a transplantable tissue with an RNAi agent in order to prevent immune-mediated rejection of transplanted tissues methods for treating a transplanted tissue(s) with an RNAi agent in order to prevent growth or propogation of latent viruses that may be present in the tissue(s)

methods for treating a transplanted tissue(s) with an RNAi agent in order to prevent apoptosis-induced ischemic injury in the tissue(s)

The instant invention also features treated transplant tissues derived by the methods of the instant invention.

Other features and advantages of the invention will be apparent from the following detailed description and claims.

BRIEF DESCRIPTION OF THE DRAWINGS

FIG. 4A depicts fluorescent images depicting untreated control, 50 nM, and 400 nM Cy-3-siRNA transfected samples. Right panel shows islets under red fluorescence. Image magnification=200×. FIG. 4B depicts a FACS analysis showing siRNA transfection efficiency in primary islets after liposomal transfection with FITC-labeled Luc-siRNA. Single cell suspensions were made after 48 hours in culture. The upper panel is untreated control sample, the middle panel from 50 nm siRNA and bottom panel from 400 nM siRNA. The value in the upper gate represents percent of FITC-positive cells (Comp-FL-1, Y-axis) versus forward scatter (FSC-H, X-axis) FIG. 4C depicts normalized real-time PCR data showing percent Ins2 expression levels among the different concentrations of (■) Ins2-siRNA treated islet samples compared to (□) non-specific siRNA control (Luc-siRNA) and (▨) untreated control samples. PCR performed in triplicate (n=3, bar graph of average with standard deviations shown. T-test P values shown with asterisks, [*]=P<0.05, [**]=P<0.005.

FIG. 5A shows fluorescent images revealing Cy-3 siRNA incorporation into isolated islets after intravenous tail vein injection (100 μg). Left panel shows islets under visible light and right panel under red fluorescence. Upper panel: Control PBS-treated islets pooled from 3 BALB/c mice not receiving siRNA. Middle and Lower panel: Isolated islets from 3 BALB/c mice receiving Cy3-Luc-siRNA. Isolated islets were dispensed into wells of a 48 well plate, cultured for 16 hours, and observed under fluorescence. Image magnification=200×. FIG. 5B depicts FACS analysis showing siRNA transfection efficiency in isolated islets after i.v. tail vein administration of FITC-labeled Luc-siRNA (100 μg). Single cell suspensions were made after overnight culture. The FACS plots show the upper panel is the untreated control sample and the bottom panel is from the FITC-Luc-siRNA treated islets. The value in the upper gate represents percent of FITC-positive cells (Comp-FL-1, Y-axis) versus forward scatter (FSC-H, X-axis) FIG. 5C. shows quantitative RT-PCR and demonstrates in vivo siRNA function in pancreatic islets. Bar graph showing normalized real-time PCR data showing the percent Ins2 expression levels from (▨) islets pooled from control treated, (□) Ins2-siRNA treated, and (■) non-specific siRNA control treated BALB/c mice. Samples were run in triplicate n=3 with standard deviation (SD) and student t-test P value shown with asterisk, [*]=(P<0.05).

DETAILED DESCRIPTION

Figure 1:
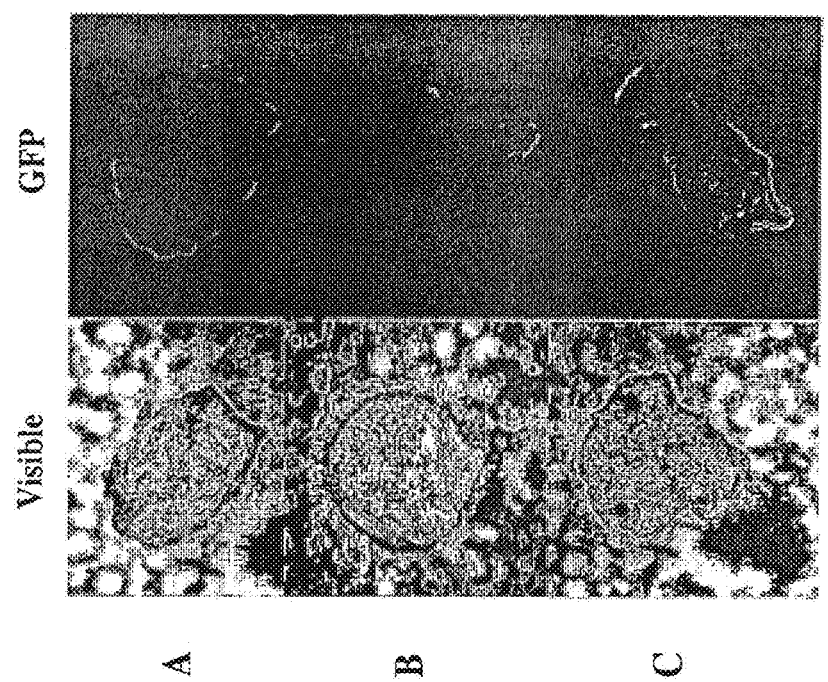
FIG. 1 shows the result of efficacious administration of anti-GFP siRNA to islet cells ex vivo. Panel A depicts images for cells that were left untreated, while panel B cells were administered anti-GFP siRNA and cells in panel C were treated with non-specific siRNA. All cells were transfected with adeno-GFP (at an M.O.I. of 500:1 viral PFU/islet) following treatment, and fluorescence was then examined.

The present invention relates, at least in part, to the discovery of methods and compositions capable of effectively delivering an RNAi agent (in preferred aspects of the invention, an siRNA) to a transplantable tissue. Administration of RNAi agents by the methods and compositions of the instant invention offers a safe, efficacious means of combating a variety of issues that can produce suboptimal transplant outcomes. Such issues primarily include: organ rejection; reactivation of latent and persistent viruses in transplanted tissues; and ischemic injury that induces apoptotic cell death in the transplanted tissue, as described in detail above. Each of these issues are addressed by the present invention through delivery to the transplanted tissue of RNAi agents capable of inhibiting: 1) production or localization of cell surface proteins that trigger immune-mediated rejection (e.g., MHC class II and class I genes); 2) growth or propogation of viruses (e.g., herpesvirus (e.g., herpes simplex, varicella-zoster virus, Epstein-Barr virus, cytomegalovirus (CMV)), hepatitis C, HIV, JC virus) that might be harbored within the transplanted tissue; and 3) molecular triggers of apoptosis activated in response to ischemic injury. As shown in the experimental data of the instant invention, delivery of such RNAi agents can be achieved by contacting tissues (e.g., cells, cell lines, organ sections, whole organs, etc.) directly with "naked" RNAi agents; or in preferred embodiments, RNAi agents in lipid-mediated delivery vehicles (e.g., liposome) and other art-recognized methods of introducing nucleotide-based agents to cells or tissues are employed. In preferred embodiments of the instant invention, such RNAi agents are administered or delivered to the transplantation tissue through perfusion, injection, or other contact with the transplant tissue prior to completion of the transplantation process with delivery of the tissue to a recipient subject.

In one aspect of the invention, a tissue is prepared for transplantation by exposing the tissue to an RNAi agent capable of downmodulating a trait of allograft rejection, such that the tissue is more suitable for transplantation as compared to an untreated tissue.

In a related aspect of the instant invention, a tissue is prepared for transplantation by exposing the tissue to an RNAi agent capable of downmodulating a trait of suboptimal allograft transplantation, such that the tissue is more suitable for transplantation as compared to an untreated tissue.

In an additional aspect of the instant invention, a tissue is prepared for transplantation by exposing the tissue to an RNAi agent capable of downmodulating an oncogene, such that the tissue is more suitable for transplantation as compared to an untreated tissue. In a related embodiment, a tissue is prepared for transplantation by exposing the tissue to an RNAi agent capable of modulating a tumor suppressor gene, such that the tissue is more suitable for transplantation as compared to an untreated tissue.

In certain preferred embodiments of the instant invention, the RNAi agent is administered to the tissue through the vasculature of the tissue.

In additional preferred embodiments, the RNAi agent is perfused into the tissue.

In other embodiments of the invention, the RNAi agent is administered to the tissue through injection into the tissue.

In an additional embodiment of the instant invention, the RNAi agent is present in a solution in which the tissue is bathed.

In other embodiments, the transplant tissue is an organ.

In certain embodiments, the tissue is an allograft.

In a preferred embodiment of the invention, the transplant tissue is of pancreatic origin; and in an additional preferred embodiment, the transplant tissue comprises β-islet cells.

In specific embodiments of the instant invention, exposure of the transplant tissue to the RNAi agent is performed in vivo. Alternatively, in other embodiments of the instant invention, exposure to the RNAi agent is performed ex vivo.

In certain embodiments, the RNAi agent is administered in a solution that additionally comprises saline.

In specific embodiments, the solution in which the RNAi agent is administered additionally comprises an immunosuppressant.

In other embodiments, the solution in which the RNAi agent is administered additionally comprises a cancer treatment.

In specific embodiments, the solution containing the RNAi agent additionally comprises a leukemia treatment.

In another embodiment, the RNAi agent is an siRNA molecule.

In a specific embodiment, the siRNA molecule is a single stranded siRNA (ss-siRNA) molecule; and in one additional embodiment, the ss-siRNA molecule is modified such that the ss-siRNA molecule has increased in situ or in vivo stability as compared to an unmodified ss-siRNA molecule (refer to WO04/014933, the entirety of which is incorporated herein by reference; Schwarz, D. S., et al. *Mol. Cell,* 2002 10, 537-548).

In a separate embodiment, the siRNA molecule is a ds-siRNA molecule.

In one embodiment, the RNAi agent comprises an oligonucleotide comprising a modification selected from the group consisting of the 2'-OH group replaced by a H, alkoxy or OR, halogen, SH, SR, amino (such as NH2, NHR, NR2), or CN group, wherein R is lower alkyl, alkenyl, alkynyl, or aryl.

In a specific embodiment, the RNAi agent comprises a 2'-O-methyl oligonucleotide.

In an additional embodiment, the RNAi agent modulates a glucose-activated insulin response.

In another embodiment, the RNAi agent enhances the fitness of a cell or tissue. In a related embodiment, the cell or tissue comprises a β-islet cell.

In an additional embodiment, the RNAi agent is exposed to the tissue through lipid-mediated delivery.

In a related embodiment, the RNAi agent is exposed to the tissue as a component of a liposomal preparation.

In another embodiment, the RNAi agent is exposed to the tissue using electroporation.

In other embodiments, the RNAi agent is directed against a major histocompatibility complex class II (MHC II) gene.

In a related embodiment, the RNAi agent downregulates expression of an MHC II gene.

In another related embodiment, the RNAi agent causes decreased production of an MHC II gene product.

In other related embodiments, the RNAi agent alters cellular localization of an MHC II gene product.

In an additional related embodiment, the RNAi agent impedes delivery of an MHC II gene product to the cell surface.

In another embodiment, the RNAi agent is directed against a major histocompatibility complex class I (MHC I) gene.

In a related embodiment, the RNAi agent causes decreased production of an MHC I gene product.

In another related embodiment, the RNAi agent downregulates expression of an MHC I gene.

In an additional related embodiment, the RNAi agent alters cellular localization of an MHC I gene product.

In another related embodiment, the RNAi agent impedes delivery of an MHC I gene product to the cell surface.

In other embodiments, the RNAi agent modulates expression of a gene involved in the apoptotic signaling pathway.

In a related embodiment, the RNAi agent inhibits expression of a gene that initiates apoptosis.

In another embodiment, the RNAi agent inhibits the growth of a virus.

In a related embodiment, the RNAi agent inhibits the replication of a virus.

In another embodiment, the RNAi agent inhibits the expression of a viral gene.

In an additional embodiment, the RNAi agent modulates host genes that modulate viral replication.

In a related embodiment, the RNAi agent inhibits host genes that promote viral replication.

In other embodiments, the virus is selected from the following: herpes simplex virus type 1 (HSV-1), and herpes simplex virus type 2 (HSV-2), cytomegalovirus (CMV), Epstein-Barr virus (EBV), Human Herpesvirus-6, Human Herpesvirus-7, and BK polyomavirus.

In a specific embodiment, the virus is HSV-1.

In another embodiment, the virus is HSV-2.

In an additional embodiment, the virus is CMV.

In another embodiment, the virus is EBV.

In one embodiment, the virus is hepatitis C.

In an additional embodiment, the virus is HIV.

In one embodiment, the virus is Human Herpesvirus-6.

In an additional embodiment, the virus is Human Herpesvirus-7.

In another embodiment, the virus is BK polyomavirus.

In one embodiment, the RNAi agent acts as an antimicrobial or antibacterial agent.

In other embodiments, the RNAi agent downregulates a gene selected from the following: ABLI, BCLI, BCL2, BCL6, CBFA2, CBL, CSFIR, ERBA, ERBB, EBRB2, ETSI, ETSI, ETV6, FGR, FOS, FYN, HCR, HRAS, JUN, KRAS, LCK, LYN, MDM2, MLL, MYB, MYC, MYCLI, MYCN, NRAS, PIM I, PML, RET, SRC, TALI, TCL3, and YES.

In another aspect of the instant invention, diabetes is treated in a transplanted tissue by exposing an RNAi agent that targets genes involved in diabetes to the tissue to be transplanted.

In additional embodiment of the instant invention, more than one RNAi agent is administered to the transplanted tissue.

In certain embodiments, treatment with RNAi agent is performed on a vertebrate animal tissue.

In one embodiment, treatment with RNAi agent is performed on a mammalian tissue.

In another embodiment, treatment with RNAi agent is performed on a non-human mammalian tissue.

In an additional embodiment, treatment with RNAi agent is performed on a pig or porcine tissue.

In a specific embodiment, treatment with RNAi agent is performed on a mouse or mouse tissue.

In another embodiment, treatment with RNAi agent is performed on a monkey or monkey tissue.

In a related embodiment, treatment with RNAi agent is performed on an animal or tissue therefrom selected from the following: baboon, chimpanzee, and orangutan.

In another embodiment, treatment with RNAi agent is performed on a human.

In an additional embodiment, treatment with RNAi agent is performed on a human tissue.

In another aspect of the instant invention, tissue prepared by the methods of the instant invention is claimed.

In an additional embodiment of the instant invention, a composition for treating allograft rejection comprising an RNAi agent that targets a major histocompatibility class II gene is claimed.

A particular aspect of the invention relates, at least in part, to use of RNA interference as mediated by short-interfering RNA (siRNA) as a non-viral means to silence genes in tissue. Little data exists about gene therapy using siRNA in pancreas tissue (or in many other tissues). To determine if siRNA treatment can silence an endogenous gene in pancreatic islets, a murine model was developed using the endocrine pancreas. In this model, the Insulin 2 (Ins2) gene was targeted with siRNA and quantitative RT-PCR, fluorescent microscopy, and FACS were used to measure transcript levels and siRNA cellular uptake and transfection efficiency. Isolated pancreatic islets were transfected with siRNA in vitro using a liposomal delivery method in a dose titration (50-400 nM) or pooled from BALB/c mice having received siRNA (100 µg) via hydrodynamic tail vein injection. In these assays, the Ins2 transcript level was significantly reduced by 55% in vitro, with FACS data showing a transfection efficiency over 45% with the 400 nM concentration. In vivo delivery of siRNA to pancreatic islets revealed a 33% reduction in Ins2 mRNA levels, while siRNA was able to be detected in 19% of isolated islet cells. Thus, RNA interference was successfully used to silence an endogenous, tissue specific gene (Ins2) in pancreatic islets when transfected in vitro or administered in vivo.

So that the invention may be more readily understood, certain terms are first defined.

The term "a trait of allograft rejection", as used herein, refers to any characteristic or activity, process or pathway involved in producing, or symptomatic of, immune-mediated rejection of a transplanted tissue.

The term "a trait of suboptimal allograft transplantation", as used herein, refers to any characteristic or activity, process or pathway involved in, or symptomatic of, creating any dangerous, toxic, or otherwise problematic outcome during tissue transplantation. In preferred embodiments of the instant invention, such traits include, e.g., immune-mediated rejection, transmission of growth- or propogation-competent virus present in the transplanted tissue, and induction of apoptosis mediated by ischemic injury to the transplanted tissue.

As used herein, the term "oncogene" refers to a gene, the aberrant expression or activity of which stimulates cell growth (e.g., abnormal cell growth). When the level of expression or activity of an oncogene in a cell is reduced, the rate of cell growth can be reduced or the cell made quiescent. In the context of the present invention, oncogenes include intracellular proteins, as well as extracellular growth factors which may stimulate cell proliferation through autocrine or paracrine function. Examples of human oncogenes against which RNAi agents can designed include c-myc, c-myb, mdm2, PKA-I (protein kinase A type I), Abl-1, Bcl2, Ras, c-Raf kinase, CDC25 phosphatases, cyclins, cyclin dependent kinases (cdks), telomerase, PDGF/sis, erb-B, fos, jun, mos, and src, to name but a few. In the context of the present invention, oncogenes also include a fusion gene resulted from chromosomal translocation, for example, the Bcr/Abl fusion oncogene.

The term "RNA" or "RNA molecule" or "ribonucleic acid molecule" refers to a polymer of ribonucleotides. The term "DNA" or "DNA molecule" or deoxyribonucleic acid molecule" refers to a polymer of deoxyribonucleotides. DNA and RNA can be synthesized naturally (e.g., by DNA replication or transcription of DNA, respectively). RNA can be post-transcriptionally modified. DNA and RNA can also be chemically synthesized. DNA and RNA can be single-stranded (i.e., ssRNA and ssDNA, respectively) or multi-stranded (e.g., double stranded, i.e., dsRNA and dsDNA, respectively). "mRNA" or "messenger RNA" is single-stranded RNA that specifies the amino acid sequence of one or more polypeptide chains. This information is translated during protein synthesis when ribosomes bind to the mRNA.

The term "nucleoside" refers to a molecule having a purine or pyrimidine base covalently linked to a ribose or deoxyribose sugar. Exemplary nucleosides include adenosine, guanosine, cytidine, uridine and thymidine. The term "nucleotide" refers to a nucleoside having one or more phosphate groups joined in ester linkages to the sugar moiety. Exemplary nucleotides include nucleoside monophosphates, diphosphates and triphosphates. The terms "polynucleotide" and "nucleic acid molecule" are used interchangeably herein and refer to a polymer of nucleotides joined together by a phosphodiester linkage between 5' and 3' carbon atoms.

The term "RNA interference" or "RNAi" (also referred to in the art as "gene silencing" and/or "target silencing", e.g., "target mRNA silencing"), as used herein, refers generally to a sequence-specific or selective process by which a target molecule (e.g., a target gene, protein or RNA) is downregulated. In specific embodiments, the process of "RNA interference" or "RNAi" features degradation of RNA molecules, e.g., RNA molecules within a cell, said degradation being triggered by an RNAi agent. Degradation is catalyzed by an enzymatic, RNA-induced silencing complex (RISC). RNAi occurs in cells naturally to remove foreign RNAs (e.g., viral RNAs). Natural RNAi proceeds via fragments cleaved from free dsRNA which direct the degradative mechanism to other similar RNA sequences. Alternatively, RNAi can be initiated by the hand of man, for example, to silence the expression of target genes.

The term "RNAi agent", as used herein, refers to an RNA (or analog thereof), having sufficient sequence complementarity to a target RNA (i.e., the RNA being degraded) to direct RNAi. An RNAi agent having a "sequence sufficiently complementary to a target RNA sequence to direct RNAi" means that the RNAi agent has a sequence sufficient to trigger the destruction of the target RNA by the RNAi machinery (e.g., the RISC) or process. An RNAi agent having a "sequence sufficiently complementary to a target RNA sequence to direct RNAi" is also intended to mean that the RNAi agent has a sequence sufficient to trigger the translational inhibition of the target RNA by the RNAi machinery or process.

As used herein, the term "small interfering RNA" ("siRNA") (also referred to in the art as "short interfering RNAs") refers to an RNA (or RNA analog) comprising between about 10-50 nucleotides (or nucleotide analogs) which is capable of directing or mediating RNA interference. Preferably, an siRNA comprises between about 15-30 nucleotides or nucleotide analogs, more preferably between about 16-25 nucleotides (or nucleotide analogs), even more preferably between about 18-23 nucleotides (or nucleotide analogs), and even more preferably between about 19-22 nucleotides (or nucleotide analogs) (e.g., 19, 20, 21 or 22 nucleotides or nucleotide analogs).

As used herein, the term "microRNA" ("miRNA") refers to an RNA (or RNA analog) comprising the product of an endogenous, non-coding gene whose precursor RNA transcripts can form small stem-loops from which mature miRNAs are cleaved by Dicer (Lagos-Quintana et al., 2001; Lau et al., 2001; Lee and Ambros, 2001; Lagos-Quintana et al., 2002; Mourelatos et al., 2002; Reinhart et al., 2002; Ambros et al., 2003; Brennecke et al., 2003; Lagos-Quintana et al., 2003; Lim et al., 2003a; Lim et al., 2003b). miRNAs are encoded in genes distinct from the mRNAs whose expression they control. Mature miRNAs represent the single stranded product of Dicer cleavage that then function as guide RNA fragments when incorporated into the RISC complex.

As used herein, the term "antisense strand" of an siRNA or RNAi agent refers to a strand that is substantially complementary to a section of about 10-50 nucleotides, e.g., about 15-30, 16-25, 18-23 or 19-22 nucleotides of the mRNA of the gene targeted for silencing. The antisense strand has sequence sufficiently complementary to the desired target mRNA sequence to direct target-specific RNA interference (RNAi), e.g., complementarity sufficient to trigger the destruction of the desired target mRNA by the RNAi machinery or process. The term "sense strand" of an siRNA or RNAi agent refers to a strand that is complementary to the antisense strand. Antisense and sense strands can also be referred to as first or second strands, the first or second strand having complementarity to the target sequence and the respective second or first strand having complementarity to said first or second strand.

As used herein, the term "guide strand" refers to a strand of an RNAi agent, e.g., an antisense strand of an siRNA duplex, that enters into the RISC complex and directs cleavage of the target mRNA. The term "guide strand" is often used interchangeably with the term "antisense strand" in the art.

A "target gene" is a gene whose expression is to be selectively inhibited or "silenced." This silencing is achieved by cleaving the mRNA of the target gene by an RNAi pathway or process.

As used herein, the term or "MHC molecule" means an MHC class I molecule and/or an MHC class II molecule.

As used herein, the term "MHC class I" or "MHC I" refers to the human Major Histocompatibility Complex class I molecules, binding peptides or genes. The human MHC region, also referred to as HLA, is found on chromosome six and includes the class I region and the class II region. Within the MHC class I region are found the HLA-A, HLA-B or HLA-C subregions for class I α chain genes. The human gene for $β_2$-microglobulin is located outside the MHC complex on a separate chromosome. As used herein, the term "MHC class I molecule" means a complex of an MHC class I α chain and a $β_2$-microglobulin chain. MHC class I molecules normally bind peptides which are generated in the cytosol and transported to the endoplasmic reticulum. After binding these peptides, the class I MHC-peptide complex is presented on the cell surface where it may be recognized by T cells. The majority of bound peptides have a length of 8-10 amino acids, although they may be as long 16 or as short as 2 (Udaka et al., (1993) *Proc. Natl. Acad. of Sci.* (USAt 90:11272-11276). See, generally, Roitt et al., eds. *Immunology* (1989) Gower Medical Publishing, London.

As used herein, the term "MHC class II" or "MHC II" refers to the human Major Histocompatibility Complex class II molecules, binding peptides or genes. The human MHC region, also referred to as HLA, is found on chromosome six and includes the class I region and the class II region. Within the MHC class II region are found the DP, DQ and DR subregions for class II α chain and β chain genes (i.e., DPα, DPβ, DQα, DQβ, DRα, and DRβ). As used herein, the term "MHC class II molecule" means a complex of an MHC class II α chain and an MHC class II β chain. MHC class II molecules normally bind peptides in an intracellular processing compartment and present these peptides on the surface of antigen presenting cells to T cells. The majority of bound peptides have a length of 13-18 amino acids but it is the peptide side chains of an approximately 9 amino acid core segment that occupy pockets of the MHC class II binding cleft and determine the specificity of binding (Brown et al., (1993) *Nature* 364:33-39; Stern et al., (1994) *Nature* 368:215-221). See, generally, Roitt et al., eds. *Immunology* (1989) Gower Medical Publishing, London.

The term "oligonucleotide" refers to a short polymer of nucleotides and/or nucleotide analogs. The term "RNA analog" refers to an polynucleotide (e.g., a chemically synthesized polynucleotide) having at least one altered or modified nucleotide as compared to a corresponding unaltered or unmodified RNA but retaining the same or similar nature or function as the corresponding unaltered or unmodified RNA. As discussed above, the oligonucleotides may be linked with linkages which result in a lower rate of hydrolysis of the RNA analog as compared to an RNA molecule with phosphodiester linkages. For example, the nucleotides of the analog may comprise methylenediol, ethylene diol, oxymethylthio, oxyethylthio, oxycarbonyloxy, phosphorodiamidate, phosphoroamidate, and/or phosphorothioate linkages. Preferred RNA analogues include sugar- and/or backbone-modified ribonucleotides and/or deoxyribonucleotides. Such alterations or modifications can further include addition of non-nucleotide material, such as to the end(s) of the RNA or internally (at one or more nucleotides of the RNA). An RNA analog need only be sufficiently similar to natural RNA that it has the ability to mediate (mediates) RNA interference.

As used herein, the "5' end", as in the 5' end of an antisense strand, refers to the 5' terminal nucleotides, e.g., between one and about 5 nucleotides at the 5' terminus of the antisense strand. As used herein, the "3' end", as in the 3' end of a sense strand, refers to the region, e.g., a region of between one and about 5 nucleotides, that is complementary to the nucleotides of the 5' end of the complementary antisense strand.

As used herein, the term "isolated RNA" (e.g., "isolated siRNA" or "isolated RNAi agent") refers to RNA molecules which are substantially free of other cellular material, or culture medium when produced by recombinant techniques, or substantially free of chemical precursors or other chemicals when chemically synthesized.

As used herein, "modulation" may constitute any alteration at any point in time of the relative activity or abundance of, for example, a gene, gene product, or pathway, as compared to wild-type levels. (Examples of such modulation include: gene knockouts, transgenic expression of a gene or mutant form of a gene, expression of a mutant form of a native gene, underexpression and overexpression of a gene.) An "RNAi modulatory compound" is therefore any compound capable of modulation in any manner of RNAi.

As used herein, a "reduced activity" is one that is at least 5% less than that of the polypeptide or protein encoded by the wild-type nucleic acid molecule or gene, preferably at least 5-10% less, more preferably at least 10-25% less and even more preferably at least 25-50%, 50-75% or 75-100% less than that of the polypeptide or protein encoded by the wild-type nucleic acid molecule or gene. Ranges intermediate to the above-recited values, e.g., 75-85%, 85-90%, 90-95%, are also intended to be encompassed by the present invention. As used herein, a "reduced activity" also includes an activity that has been deleted or "knocked out" (e.g., approximately 100% less activity than that of the polypeptide or protein encoded by the wild-type nucleic acid molecule or gene). Likewise, an "enhanced activity" is one that is at least 5% greater than that of the polypeptide or protein encoded by the wild-type nucleic acid molecule or gene, preferably at least 5-10% greater, more preferably at least 10-25% greater and even more preferably at least 25-50%, 50-75% or 75-100% greater or 100% or more greater (two-fold or greater elevated) than that of the polypeptide or protein encoded by the wild-type nucleic acid molecule or gene. Ranges intermediate to the above-recited values, e.g., 75-85%, 85-90%, 90-95%, are also intended to be encompassed by the present invention.

Activity can be determined according to any well accepted assay for measuring activity of a particular protein of interest. Activity can be measured or assayed directly, for example, by measuring an activity of a protein isolated or purified from a cell. Alternatively, an activity can be measured or assayed within a cell or in an extracellular medium or in a crude extract of cells. Additionally, activity of a targeted protein may also be measured in a whole organism.

The term "tissue", as used herein, refers to any biological entity derived from an organism (directly or via an isolated progenitor cell or population) that is comprised of cells, including whole organs, organ sections and subsections, tumor cells, cells, cell lines, etc. The term also includes plant cells, as used herein.

The term "perfusion", as used herein, refers to the act of pouring over or through, especially the passage of a fluid through the vessels of a specific organ. In specific embodiments of the instant invention, fluids containing RNAi agents are perfused through the vasculature of transplant tissues.

The terms "apoptosis" or "programmed cell death," refers to the physiological process by which unwanted or useless cells are eliminated during development and other normal biological processes. Apoptosis, is a mode of cell death that occurs under normal physiological conditions and the cell is an active participant in its own demise ("cellular suicide"). It is most often found during normal cell turnover and tissue homeostasis, embryogenesis, induction and maintenance of immune tolerance, development of the nervous system and endocrine-dependent tissue atrophy. Apoptosis may also be triggered by external events and stimuli, such as ischemic injury in the case of certain preferred embodiments of the instant invention. Cells undergoing apoptosis show characteristic morphological and biochemical features. These features include chromatin aggregation, nuclear and cytoplasmic condensation, partition of cytoplasm and nucleus into membrane-bound vesicles (apoptotic bodies) which contain ribosomes, morphologically intact mitochondria and nuclear material. In vivo, these apoptotic bodies are rapidly recognized and phagocytized by either macrophages or adjacent epithelial cells. Due to this efficient mechanism for the removal of apoptotic cells in vivo no inflammatory response is elicited. In vitro, the apoptotic bodies as well as the remaining cell fragments ultimately swell and finally lyse. This terminal phase of in vitro cell death has been termed "secondary necrosis."

"Inhibition of gene expression" refers to the absence (or observable decrease) in the level of protein and/or mRNA product from a target gene. "Specificity" refers to the ability to inhibit the target gene without manifest effects on other genes of the cell. The consequences of inhibition can be confirmed by examination of the outward properties of the cell or organism or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radiohnmunoassay (RIA), other immunoassays, and fluorescence activated cell analysis (FACS).

The term "glucose-activated insulin response", as used herein, refers to the process by which the islet cells of the pancreas sense and respond to glucose levels (e.g., circulating blood glucose levels for islet cells in vivo). High circulating blood glucose levels will typically trigger elevated production and secretion of insulin by pancreatic islet cells in vivo, through molecular signaling mechanisms that are widely recognized in the art. These glucose signaling responses may be modulated by RNAi agents (e.g., shRNA, miRNA, siRNA, etc.; Katayama, K., et al. *FEBS Lett.* 2004 560, 178-82; Huang, A., et al *FEBS Lett.* 2004 558, 69-73).

The term "loss-of-function," as it refers to genes inhibited by the subject RNAi method, refers a diminishment in the level of expression of a gene when compared to the level in the absence of RNAi agents.

A gene "involved" in a disorder includes a gene, the normal or aberrant expression or function of which effects or causes a disease or disorder or at least one symptom of said disease or disorder.

Various methodologies of the instant invention include a step that involves comparing a value, level, feature, characteristic, property, etc. to a "suitable control", referred to interchangeably herein as an "appropriate control". A "suitable control" or "appropriate control" is any control or standard familiar to one of ordinary skill in the art useful for comparison purposes. In one embodiment, a "suitable control" or "appropriate control" is a value, level, feature, characteristic, property, etc. determined prior to performing an RNAi methodology, as described herein. For example, a transcription rate, mRNA level, translation rate, protein level, biological activity, cellular characteristic or property, genotype, phenotype, etc. can be determined prior to introducing an RNAi agent of the invention into a cell or organism. In another embodiment, a "suitable control" or "appropriate control" is a value, level, feature, characteristic, property, etc. determined in a cell or organism, e.g., a control or normal cell or organism, exhibiting, for example, normal traits. In yet another embodiment, a "suitable control" or "appropriate control" is a predefined value, level, feature, characteristic, property, etc.

Various aspects of the invention are described in further detail in the following subsections.

I. The RNAi Pathway

In recent years, numerous studies have shed light on the mechanisms of RNA-mediated gene silencing. Since the discoveries of post-transcriptional gene silencing (PTGS) in plants and RNA interference (RNAi) in *C. elegans*, RNA-mediated silencing mechanisms have been identified in a variety of organisms, indicating that this gene silencing phenomenon is evolutionarily conserved. In PTGS or RNAi, the presence of double-stranded RNA (dsRNA) leads to the sequence-specific degradation of corresponding mRNA, silencing expression of a target gene having homology with the dsRNA (Hannon, G. J. *Nature*, 2002 418: 244-51; Hutvagaer and Zamore *Curr Opin Genet Dev*, 2002 12: 225-32). Studies in plants indicate that PTGS likely evolved as a primitive defense system against molecular parasites, such as viruses and transposons. As a result, there are many examples of viral factors from plant viruses that have been found to inhibit PTGS (Waterhonse, P. M., et al. *Nature*, 2001 411: 834-42; Voinnet, O. *Trends Genet*, 2001 17: 449-59). Recently, a gene product that interferes with RNAi was identified in an insect virus (Li, H., et al. Science, 2002 296: 1319-21).

The RNAi pathway is the best studied of the RNA-mediated gene silencing mechanisms. In the RNAi response, the RNase III enzyme, Dicer, cleaves double-stranded RNA (dsRNA) to produce small interfering RNAs (siRNAs). The siRNAs are 21-23 nucleotide dsRNAs with specialized features, such as a 2 base 3' overhang, 5' phosphate groups, and 3' hydroxyl groups. Acting as functional intermediates in the pathway, siRNAs are incorporated into a large enzyme complex called the RNA-induced silencing complex (RISC). Here, the siRNA functions as a guide to target the specific cleavage of mRNA, presumably by an enzyme within the complex. In plants and invertebrates, long dsRNAs can be expressed or introduced to initiate specific gene silencing (Hannon, G. J. *Nature*, 2002 418: 244-51; Hutvagaer and Zamore *Curr Opin Genet Dev*, 2002 12: 225-32). However, in mammalian cells, the introduction of long (>40 bp) dsRNA can lead to the sequence-independent activation of the interferon (IFN) response, which inhibits translation in the cell (Samuel, C. E. *Clin Microbiol Rev*, 2001 14, 778-809). In order to bypass the IFN response, siRNAs can be directly administered to cells and the desired gene-silencing effect is still achieved (Zamore, P. D., et al. *Cell*, 2000 101, 25-33; Elbashir, S. M., et al. *Nature*, 2001 411, 494-8).

In addition to cleavage of long dsRNAs, Dicer also plays an important role in development by processing micro RNAs (miRNA) from short stem loop precursors. These miRNAs have been implicated in the control of gene expression during specific stages of development. Unlike the processing of dsRNA to double-stranded siRNAs, Dicer cleaves the miRNA precursors to produce single-stranded RNA (ssRNA) molecules of 21-22 nucleotides [Hutvagaer and Zamore *Curr Opin Genet Dev*, 2002 12: 225-32; McManus, M. T. and P. A. Sharp, *Nat Rev Genet*, 2002 3, 737-47). The earliest identified miRNAs, lin-4 and let-7, were found to exert their control of gene expression by affecting the translation of mRNA. Unlike siRNAs, these miRNA did not have perfect or near-perfect (>95%) complementarity with their target RNAs. Rather than specifically degrading the mRNA, these miRNAs bound to non-identical 21-22 base sequences in the 3' untranslated region (UTR) of mRNA, thereby preventing translation (Grishok, A., et al., *Cell*, 2001 106, 23-34). Using bioinformatics approaches, several groups have found numerous examples of miRNAs in several different organisms (Lau, N. C., et al., *Science*, 2001 294, 858-62; Lagos-Quintana, M., et al, *Science*, 2001 294, 853-8; Rhoades, M. W., et al., *Cell*, 2002.110, 513-20). Intriguingly, a recent study found that a single-stranded miRNA was able to function as an siRNA, specifically degrading target sequences that bore perfect complementarity to the miRNA sequence. This study provided evidence that the degree of complementarity between a miRNA and its target sequence determined whether the miRNA would act as a translational repressor or as a guide in a RISC-like complex leading to degradation of mRNA (Hutvagner, G. and P. D. Zamore. *Science*, 2002 297, 2056-60). This in vitro finding was supported by new reports in plants, where miRNAs with perfect sequence complementarity to targets were found to specifically degrade these mRNAs (Llave, C, et al., *Science*, 2002 297, 2053-6). The application of the RNA-mediated silencing mechanisms has revolutionized genetic and functional studies of specific genes. Researchers can simply introduce long dsRNA or siRNA (depending on the species under study) to silence the expression of that gene. In mammalian systems, this has been accomplished in tissue culture settings by transfecting or electroporating siRNAs into cells (Elbashir, S. M., et al. *Nature*, 2001 411, 494-8; Jacque, J. M., et al. *Nature*, 2002 418, 435-8). Additionally, in vivo studies in mice have been carried out by injecting siRNAs into the animals (McCaffrey, A. P., et al., *Nature*, 2002 418, 38-9). RNAi is thus a powerful method for the study of gene function in animals and plants and is being developed as a therapy for treating genetic disorders and viral infections.

II. RNA Molecules and Agents

The present invention features "small interfering RNA molecules" ("siRNA molecules" or "siRNA") and methods (e.g., therapeutic methods) for using said siRNA molecules. An siRNA molecule of the instant invention is preferably a duplex consisting of a sense strand and complementary antisense strand, the antisense strand having sufficient complementarity to a target mRNA to mediate RNAi. Because only the antisense strand of an siRNA duplex incorporates into the RISC to mediate cleavage or silencing of the target mRNA, a single antisense strand capable of activating RISC (e.g., a stable form of the antisense strand) could mimic the functionality of the siRNA duplex. Preferably, the strands of an siRNA duplex are aligned such that there are at least 1, 2, or 3 bases at the end of the strands which do not align (i.e., for which no complementary bases occur in the opposing strand) such that an overhang of 1, 2 or 3 residues occurs at one or both ends of the duplex when strands are annealed. Preferably, the siRNA molecule has a length from about 10-50 or more nucleotides, i.e., each strand comprises 10-50 nucleotides (or nucleotide analogs). More preferably, the siRNA molecule has a length from about 15-45 or 15-30 nucleotides. Even more preferably, the siRNA molecule has a length from about 16-25 or 18-23 nucleotides. The siRNA molecules of the invention further have a sequence that is "sufficiently complementary" to a target mRNA sequence to direct target-specific RNA interference (RNAi), as defined herein, i.e., the siRNA has a sequence sufficient to trigger the destruction of the target mRNA by the RNAi machinery or process.

siRNAs function as the specificity determinants of the RNAi pathway, where they act as guides to direct endonucleolytic cleavage of their target RNAs (Hamilton and Baulcombe, 1999; Hammond et al., 2000; Zamore et al., 2000; Elbashir et al., 2001b). The two strands of an siRNA are not equally eligible for assembly into RISC (Schwarz et al., 2003). Rather, both the absolute and relative stabilities of the base pairs at the 5' ends of the two siRNA strands determine the degree to which each strand participates in the RNAi pathway. siRNA duplexes can be functionally asymmetric, with only one of the two strands able to trigger RNAi. Asymmetry is also the hallmark of a related class of small, single-stranded, non-coding RNAs, microRNAs (miRNAs).

In general, siRNA containing nucleotide sequences sufficiently identical to a portion of the target gene to effect RISC-mediated cleavage of the target gene are preferred. 100% sequence identity between the siRNA and the target gene is not required to practice the present invention. The invention can tolerate sequence variations within the methods, tissues and compositions of the invention in order to enhance efficiency and specificity of RNAi. For example, siRNA sequences with insertions, deletions, and single point mutations relative to the target sequence can also be effective for inhibition. Alternatively, siRNA sequences with nucleotide analog substitutions or insertions can be effective for inhibition.

The siRNAs of the invention can comprise 16-30, e.g., 16, 17, 18, 19, 20, 21, 22, 23, 24, 25, 26, 27, 28, 29, or 30 nucleotides in each strand, wherein one of the strands is substantially complementary, e.g., at least 80% complementary (or more, e.g., 85%, 90%, 95%, or 100%)(for example, having 3, 2, 1, or 0 mismatched nucleotide(s)), to a target region. A target region differs by at least one base pair between the wild type and mutant allele, e.g., a target region comprising a gain-of-function mutation, and the other strand is identical or substantially identical to the first strand. The dsRNA molecules of the invention can be chemically synthesized or can be transcribed be in vitro from a DNA template or engineered RNA precursor.

The dsRNA molecules can be designed using any method known in the art, for instance, by using the following protocol:
1. Beginning with an AUG start codon, search for AA dinucleotide sequences; each AA and the 3' adjacent 16 or more nucleotides are potential siRNA targets. The siRNA should be specific for a target region that differs by at least one base pair between the wild type and mutant allele, e.g., a target region comprising the gain-of-function mutation. In cases where the gain-of-function mutation is associated with one or more other mutations in the same gene, the siRNA can be targeted to any of the mutations. In some cases, the siRNA is targeted to an allelic region that does not comprise a known mutation but does comprise an allelic variation of the wild-type (reference) sequence. The first strand should be complementary to this sequence, and the other strand is identical or substantially identical to the first strand. In one embodiment, the nucleic acid molecules are selected from a region of the target allele sequence beginning at least 50 to 100 nt downstream of the start codon, e.g., of the sequence of Insulin 2. Further, siRNAs with lower G/C content (35-55%) may be more active than those with G/C content higher than 55%. Thus in one embodiment, the invention includes nucleic acid molecules having 35-55% G/C content. In addition, the strands of the siRNA can be paired in such a way as to have a 3' overhang of 1 to 4, e.g., 2, nucleotides. Thus in another embodiment, the nucleic acid molecules can have a 3' overhang of 2 nucleotides, such as TT. The overhanging nucleotides can be either RNA or DNA.
2. Using any method known in the art, compare the potential targets to the appropriate genome database (human, mouse, rat, etc.) and eliminate from consideration any target sequences with significant homology to other coding sequences. One such method for such sequence homology searches is known as BLAST, which is available at www.ncbi.nlm.nih.gov/BLAST.
3. Select one or more sequences that meet your criteria for evaluation. Further general information about the design and use of siRNA may be found in "The siRNA User Guide," available at http://www.mpibpc.gwdg.de/abteilungen/100/105/sirna.html. The siRNAs of the invention may have one or more modified bases in the antisense strand, e.g., U(5Br), U(5I), and/or DAP. Such modified siRNAs can be synthesized with the modified base.

Negative control siRNAs should have the same nucleotide composition as the selected siRNA, but without significant sequence complementarity to the appropriate genome. Such negative controls can be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence.

Sequence identity may be determined by sequence comparison and alignment algorithms known in the art. To determine the percent identity of two nucleic acid sequences (or of two amino acid sequences), the sequences are aligned for optimal comparison purposes (e.g., gaps can be introduced in the first sequence or second sequence for optimal alignment). The nucleotides (or amino acid residues) at corresponding nucleotide (or amino acid) positions are then compared. When a position in the first sequence is occupied by the same residue as the corresponding position in the second sequence, then the molecules are identical at that position. The percent identity between the two sequences is a function of the number of identical positions shared by the sequences (i.e., % homology=# of identical positions/total # of positions×100), optionally penalizing the score for the number of gaps introduced and/or length of gaps introduced.

The comparison of sequences and determination of percent identity between two sequences can be accomplished using a mathematical algorithm. For certain applications, the alignment can be generated over a certain portion of the sequence aligned having sufficient identity but not over portions having low degree of identity (i.e., a local alignment). A preferred, non-limiting example of a local alignment algorithm utilized for the comparison of sequences is the algorithm of Karlin and Altschul (1990) *Proc. Natl. Acad. Sci. USA* 87:2264-68, modified as in Karlin and Altschul (1993) *Proc. Natl. Acad. Sci. USA* 90:5873-77. Such an algorithm is incorporated into the BLAST programs (version 2.0) of Altschul, et al. (1990) *J. Mol. Biol.* 215: 403-10.

The alignment may also be optimized by introducing appropriate gaps and percent identity is determined over the length of the aligned sequences (i.e., a gapped alignment). To obtain gapped alignments for comparison purposes, Gapped BLAST can be utilized as described in Altschul et al., (1997) *Nucleic Acids Res.* 25(17):3389-3402. In another embodiment, the alignment is optimized by introducing appropriate gaps and percent identity is determined over the entire length of the sequences aligned (i.e., a global alignment). A preferred, non-limiting example of a mathematical algorithm utilized for the global comparison of sequences is the algorithm of Myers and Miller, *CABIOS* (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

Greater than 80% sequence identity, e.g., 80%, 81%, 82%, 83%, 84%, 85%, 86%, 87%, 88%, 89%, 90%, 91%, 92%, 93%, 94%, 95%, 96%, 97%, 98%, 99% or even 100% sequence identity, between the siRNA antisense strand and the portion of the target gene is preferred. Alternatively, the siRNA may be defined functionally as a nucleotide sequence (or oligonucleotide sequence) that is capable of hybridizing with a portion of the target gene transcript (e.g., 400 mM NaCl, 40 mM PIPES pH 6.4, 1 mM EDTA, 50° C. or 70° C. hybridization for 12-16 hours; followed by washing). Additional preferred hybridization conditions include hybridization at 70° C. in 1×SSC or 50° C. in 1×SSC, 50% formamide followed by washing at 70° C. in 0.3×SSC or hybridization at 70° C. in 4×SSC or 50° C. in 4×SSC, 50% formamide followed by washing at 67° C. in 1×SSC. The hybridization temperature for hybrids anticipated to be less than 50 base pairs in length should be 5-10° C. less than the melting temperature (Tm) of the hybrid, where Tm is determined according to the following equations. For hybrids less than 18 base pairs in length, $Tm(°C.)=2(\# of A+T bases)+4(\# of G+C bases)$. For hybrids between 18 and 49 base pairs in length, $Tm(°C.)=81.5+16.6(\log 10[Na+])+0.41(\% G+C)-(600/N)$, where N is the number of bases in the hybrid, and [Na+] is the concentration of sodium ions in the hybridization buffer ([Na+] for 1×SSC=0.165 M). Additional examples of stringency conditions for polynucleotide hybridization are provided in Sambrook, J., E. F. Fritsch, and T. Maniatis, 1989, *Molecular Cloning: A Laboratory Manual*, Cold Spring Harbor Laboratory Press, Cold Spring Harbor, N.Y., chapters 9 and 11, and *Current Protocols in Molecular Biology*, 1995, F. M. Ausubel et al., eds., John Wiley & Sons, Inc., sections 2.10 and 6.3-6.4, incorporated herein by reference. The length of the identical nucleotide sequences may be at least about 10, 12, 15, 17, 20, 22, 25, 27, 30, 32, 35, 37, 40, 42, 45, 47 or 50 bases.

The RNA molecules of the present invention can be modified to improve stability in serum or in medium for cell and/or organ cultures. In order to enhance the stability, the 3'-residues may be stabilized against degradation, e.g., they may be selected such that they consist of purine nucleotides, particularly adenosine or guanosine nucleotides. Alternatively, substitution of pyrimidine nucleotides by modified analogues, e.g., substitution of uridine by 2'-deoxythymidine is tolerated and does not affect the efficiency of RNA interference.

In a preferred aspect, the invention features small interfering RNAs (siRNAs) that include a sense strand and an antisense strand, wherein the antisense strand has a sequence sufficiently complementary to a target mRNA sequence to direct target-specific RNA interference (RNAi) and wherein the sense strand and/or antisense strand is modified by the substitution of internal nucleotides with modified nucleotides, such that in vivo stability is enhanced as compared to a corresponding unmodified siRNA.

RNA molecules of the invention may additionally contain at least one modified nucleotide analogue. The nucleotide analogues may be located at positions where the target-specific activity, e.g., the RNAi mediating activity is not substantially effected, e.g., in a region at the 5'-end and/or the 3'-end of the RNA molecule. Particularly, the ends may be stabilized by incorporating modified nucleotide analogues.

Preferred nucleotide analogues include sugar- and/or backbone-modified ribonucleotides (i.e., include modifications to the phosphate-sugar backbone). For example, the phosphodiester linkages of natural RNA may be modified to include at least one of a nitrogen or sulfur heteroatom. In preferred backbone-modified ribonucleotides the phosphoester group connecting to adjacent ribonucleotides is replaced by a modified group, e.g., of phosphothioate group. In preferred sugar-modified ribonucleotides, the 2' OH-group is replaced by a group selected from H, OR, R, halo, $SH$, $SR$, $NH_2$, $NHR$, $NR_2$ or $ON$, wherein R is $C_1$-$C_6$ alkyl, alkenyl or alkynyl and halo is F, Cl, Br or I. Exemplary art-recognized modifications of RNAi agents include, e.g., 2-Fluoro and 2-Chloro modifications and other stabilizing modifications, such as 2'-O-Me modifications and locked nucleic acids (LNA).

Also preferred are nucleobase-modified ribonucleotides, i.e., ribonucleotides, containing at least one non-naturally occurring nucleobase instead of a naturally occurring nucleobase. Bases may be modified to block the activity of adenosine deaminase. Exemplary modified nucleobases include, but are not limited to, uridine and/or cytidine modified at the 5-position, e.g., 5-(2-amino)propyl uridine, 5-bromo uridine; adenosine and/or guanosines modified at the 8 position, e.g., 8-bromo guanosine; deaza nucleotides, e.g., 7-deaza-adenosine; O- and N-alkylated nucleotides, e.g., N6-methyl adenosine are suitable. It should be noted that the above modifications may be combined.

Additional modified and conjugated forms of RNAi agents may also be used in the methods of the present invention, including, e.g., cholesterol conjugation, as such modification has been found to significantly improve in vivo pharmacological properties (Soutschek J, et al. *Nature* 2004 432: 173-78).

RNA may be produced enzymatically or by partial/total organic synthesis, any modified nibonucleotide can be introduced by in vitro enzymatic or organic synthesis. In one embodiment, an RNAi agent is prepared chemically. Methods of synthesizing RNA molecules are known in the art, in particular, the chemical synthesis methods as de scribed in Verma and Eckstein (1998) *Annul Rev. Biochem.* 67:99-134. In another embodiment, an RNAi agent (e.g. a siRNA) is prepared enzymatically. For example, a ds-siRNA can be prepared by enzymatic processing of a long ds RNA having sufficient complementarity to the desired target mRNA. Processing of long ds RNA can be accomplished in vitro, for example, using appropriate cellular lysates and ds-siRNAs can be subsequently purified by gel electrophoresis or gel filtration. ds-siRNA can then be denatured according to art-recognized methodologies. In an exemplary embodiment, RNA can be purified from a mixture by extraction with a solvent or resin, precipitation, electrophoresis, chromatography, or a combination thereof. Alternatively, the RNA may be used with no or a minimum of purification to avoid losses due to sample processing. Alternatively, the siRNA can also be prepared by enzymatic transcription from synthetic DNA templates or from DNA plasmids isolated from recombinant bacteria. Typically, phage RNA polymerases are used such as T7, T3 or SP6 RNA polymerase (Milligan and Uhlenbeck (1989) *Methods Enzymol.* 180:51-62). The RNA may be dried for storage or dissolved in an aqueous solution. The solution may contain buffers or salts to inhibit annealing, and/or promote stabilization of the single strands.

The instant invention additionally provides for delivery of shRNAs having enhanced specificity or efficacy in mediating RNAi. In contrast to short siRNA duplexes, short hairpin RNAs (shRNAs) mimic the natural precursors of miRNAs and enter at the top of the RNAi pathway. For this reason, shRNAs are believed to mediate RNAi more efficiently by being fed through the entire natural RNAi pathway.

shRNAs have a single strand that forms a duplex stem including two portions that are generally complementary, and a loop, that connects the two portions of the stem. In a preferred embodiment, short hairpin RNAs of the invention are artificial constructs engineered to deliver desired siRNAs.

In shRNAs employed in certain embodiments of the instant invention, one portion of the duplex stem is a nucleic acid sequence that is complementary (or antisense) to the target mRNA. Thus, shRNAs include a duplex stem with two portions and a loop connecting the two stem portions. The two stem portions are about 18 or 19 to about 25, 30, 35, 37, 38, 39, or 40 or more nucleotides in length. When used in mammalian cells, the length of the stem portions should be less than about 30 nucleotides to avoid provoking non-specific responses like the interferon pathway. In non-mammalian cells, the stem can be longer than 30 nucleotides. In fact, the stem can include much larger sections complementary to the target mRNA (up to, and including the entire mRNA). The two portions of the duplex stem must be sufficiently complementary to hybridize to form the duplex stem. Thus, the two portions can be, but need not be, fully or perfectly complementary. In addition, the two stem portions can be the same length, or one portion can include an overhang of 1, 2, 3, or 4 micleotides. The overhanging nucleotides can include, for example, uracils (Us), e.g., all Us. The loop in the shRNAs can be 2, 3, 4, 5, 6, 7, 8, 9, or more, e.g., 15 or 20, or more nucleotides in length.

shRNAs of the invention include the sequences of the desired siRNA duplex. The desired siRNA duplex, and thus both of the two stem portions in the shRNA, are selected by methods known in the art.

The shRNAs of the invention can be synthesized by standard methods known in the art, e.g., by use of an automated DNA synthesizer (such as are commercially available from Biosearch, Applied Biosystems, etc.). The shRNAs can be used directly as described below or cloned into expression cassettes or vectors by methods known in the field.

Such cassettes or vectors can be constructed by recombinant DNA technology methods known in the art. Vectors can be plasmid, viral, or other vectors known in the art such as those described herein, used for replication and expression in mammalian cells or other targeted cell types. The nucleic acid sequences encoding the shRNAs of the invention can be prepared using known techniques. For example, two synthetic DNA oligonucleotides can be synthesized to create a novel gene encoding the entire shRNA. The DNA oligonucleotides, which will pair, leaving appropriate 'sticky ends' for cloning, can be inserted into a restriction site in a plasmid that contains a promoter sequence (e.g., a Pol II or a Pol III promoter) and appropriate terminator sequences 3' to the shRNA sequences (e.g., a cleavage and polyadenylation signal sequence from SV40 or a Pol III terminator sequence).

The invention also encompasses cells that contain any of the foregoing expression vectors and thereby express the nucleic acid molecules of the invention in the cell. The cells can be cultured using known techniques and methods (see, e.g., Culture of Animal Cells (R. I. Freshney, Alan R. Liss, Inc. 1987); Molecular Cloning, Sambrook et al. (Cold Spring Harbor Laboratory Press, 1989)).

The expression of the shRNAs of certain embodiments of the invention is driven by regulatory sequences, and the vectors of the invention can include any regulatory sequences known in the art to act in mammalian cells. The term regulatory sequence includes promoters, enhancers, and other expression control elements. A person skilled in the art would be able to choose the appropriate regulatory sequence.

The regulatory sequences can be inducible or constitutive. Suitable constitutive regulatory sequences include the regulatory sequence of a housekeeping gene such as the α-actin regulatory sequence, or may be of viral origin such as regulatory sequences derived from mouse mammary tumor virus (MMTV) or cytomegalovirus (CMV).

Alternatively, the regulatory sequence can be selected to direct expression in specific organs or cell types (see, e.g., Lasko et al., 1992, *Proc. Natl. Acad. Sci. USA* 89:6232). Several tissue-specific regulatory sequences are known in the art including the albumin regulatory sequence for liver (Pinkert et al., 1987, *Genes Dev.* 1:268276); the endothelin regulatory sequence for endothelial cells (Lee, 1990, *J. Biol. Chem.* 265:10446-50); the keratin regulatory sequence for epidermis; the myosin light chain-2 regulatory sequence for heart (Lee et al., 1992, *J. Biol. Chem.* 267:15875-85), and the insulin regulatory sequence for pancreas (Bucchini et al., 1986, *Proc. Natl. Acad. Sci. USA* 83:2511-2515), or the vav regulatory sequence for hematopoietic cells (Oligvy et al., 1999, *Proc. Natl. Acad. Sci. USA* 96:14943-14948). Another suitable regulatory sequence, which directs constitutive expression of transgenes in cells of hematopoietic origin, is the murine MHC class I regulatory sequence (Morello et al., 1986, *EMBO J.* 5:1877-1882). Since NMC expression is induced by cytokines, expression of a test gene operably linked to this regulatory sequence can be upregulated in the presence of cytokines.

In addition, expression of a transgene encoding an shRNA can be precisely regulated, for example, by using an inducible regulatory sequence and expression systems such as a regulatory sequence that is sensitive to certain physiological regulators, e.g., circulating glucose levels, or hormones (Docherty et al., 1994, FASEB J. 8:20-24). Such inducible expression systems, suitable for the control of transgene expression in cells or in mammals such as mice, include regulation by ecdysone, by estrogen, progesterone, tetracycline, chemical inducers of dimerization, and isopropyl-beta-D1-thiogalactopyranoside (IPTG) (collectively referred to as "the regulatory molecule'). Each of these expression systems is well described in the literature and permits expression of the transgene throughout the animal in a manner controlled by the presence or absence of the regulatory molecule. Such expression systems can be employed, e.g., during transplantation of tissues of transgenic animals. For a review of inducible expression systems, see, e.g., Mills, 2001, *Genes Devel.* 15:1461-1467, and references cited therein.

The regulatory elements referred to above include, but are not limited to, the cytomegalovirus hCMV immediate early gene, the early or late promoters of SV40 adenovirus (Bernoist et al., *Nature,* 290:304, 1981), the tet system, the lac system, the system, the TAC system, the TRC system, the major operator and promoter regions of phage λ, the control regions of fd coat protein, the promoter for 3-phosphoglycerate kinase, the promoters of acid phosphatase, and the promoters of the yeast aha-mating factors. Additional promoters include the promoter contained in the 3' long terminal repeat of Rous sarcoma virus (Yamamoto et al., *Cell* 22:787-797, 1988); the herpes thymidine kinase promoter (Wagner et al., *Proc. Natl. Acad. Sci. USA* 78:1441, 1981); or the regulatory sequences of the metallothionein gene (Brinster et al., *Nature* 296:39, 1988).

RNAi agents of the invention (e.g., siRNAs, shRNAs) can be synthesized in vivo, in situ, or in vitro. Endogenous RNA polymerase of the cell may mediate transcription in vivo or in situ, or cloned RNA polymerase can be used for transcription in vivo or in vitro. For transcription from a transgene in vivo or an expression construct, a regulatory region (e.g., promoter, enhancer, silencer, splice donor and acceptor, polyadenylation) may be used to transcribe the RNAi agent (e.g. a siRNA). Inhibition may be targeted by specific transcription in an organ, tissue, or cell type; stimulation of an environmental condition (e.g., infection, stress, temperature, chemical inducers); and/or engineering transcription at a developmental stage or age. A transgenic organism that expresses an RNAi agent (e.g. a siRNA) from a recombinant construct may be produced by introducing the construct into a zygote, an embryonic stem cell, or another multipotent cell derived from the appropriate organism.

RNAi agents and the constructs encoding the RNAi agents of the instant invention can also be delivered to transplanted tissues by employing adenovirus and other art-recognized systems for gene therapy. Such systems can be implemented with the methods, tissues and compositions of the instant invention to deliver RNAi agents, e.g., to humans.

III. RNAi Targets

The present invention features methods and compositions for the manipulation of gene expression in transplantable cells and/or tissues. In certain embodiments, the invention features the delivery of siRNA both in vivo and in vitro to silence expression of one or more target genes. The compositions and methods of the invention are particularly suited for altering the phenotype of transplantable cells and/or tissues. For example, manipulation of gene expression levels at the time of cell and/or tissue procurement and/or isolation could serve to enhance the survival and function of the cells and/or tissue and could result in greater clinical success in further transplantation of said cells or tissues. Moreover, siRNA is a non-viral method of altering gene expression and thus would be preferred for immunosuppressed transplant patients.

In certain embodiments, the invention features delivery of siRNA during or through the procurement of an organ (e.g., via administration via the vasculature of said organ) and during or through isolation of transplantable cells from said organ. siRNA-mediated gene therapy can be applied in several instances during the organ procurement process: 1) pre-procurement via intravenous perfusion in the deceased donor; 2) via organ perfusion prior to packaging for transport; and/or 3) in cell culture, for example, in the case of islet transplantation. The methods and compositions of the invention may therefore be applied in any combination with procurement of an organ and/or tissue, e.g., siRNA may be used to alter phenotype prior to procurement of an organ or tissue and/or siRNA may be used to alter phenotype of an organ or tissue following procurement.

The methods and compositions of the invention may be applied to any organ and/or tissue to change the phenotype of that organ and/or tissue. For example, the methods and compositions of the invention may be applied to treatment of cytomegalovirus (CMV) in transplantable tissue, e.g., to alter virus replication or otherwise inhibit propagation of this virus, which is commonly a latent infection found in transplantable organs and/or tissues. The methods and compositions of the invention may also be used, e.g., to treat or prevent hepatitis C in liver tissues prior to and/or during transplantation, as transmission of hepatitis C presents a common and important problem for liver transplantation.

The methods and compositions of the invention may also be applied during oncology treatments, e.g., during surgical oncology. For example, RNAi agents may be administered using the methods of the invention for purpose of inhibiting replication of aberrant (e.g., tumor) cells. Inhibition of cell cycle genes and other such genes vital to tumor propagation can enhance oncology treatments.

In preferred aspects of the invention, the target mRNA molecule of the invention specifies the amino acid sequence of a protein associated with a deleterious outcome of organ transplantation, which most commonly can include proteins associated with organ rejection, proteins associated with a viral infection and/or pathological condition, and proteins associated with the process of apoptosis/cell death.

The MHC genes may be targeted in combatting tissue rejection. In preferred embodiments of the instant invention, the gene targeted by the RNAi agent encodes for an MHC molecule characteristic of the grafted tissue. For MHC class II genes, any of the genes of the DP, DQ and DR subregions for class II α chain and β chain genes (i.e., DPα, DPβ, DQα, DQβ, DRα, and DRβ) can be targeted. Similarly, in certain embodiments of the instant invention, MHC class I genes are targeted, including any of the genes in the HLA-A, HLA-B or HLA-C subregions for class I α chain genes, or $\beta_2$-microglobulin (located outside the MHC complex on a separate chromosome in humans) may also be targeted. Prevention of organ rejection may also be achieved by approaches comprising direct targeting of genes encoding for proteins associated with T cell activity and of genes encoding for proteins associated with appropriate expression, processing, trafficking and/or delivery/cellular localization of, e.g., MHC gene products and T cell gene products associated with organ rejection. In addition, adhesion molecules (e.g., CTLA-4) may also be targeted to inhibit tissue rejection by the methods and compositions of the instant invention.

In certain embodiments of the invention, the target gene(s) encode for a protein that may be a pathogen-associated protein (e.g., a viral protein involved in immunosuppression of the host, replication of the pathogen, transmission of the pathogen, or maintenance of the infection), or a host protein which facilitates entry of the pathogen into the host, drug metabolism by the pathogen or host, replication or integration of the pathogen's genome, establishment or spread of infection in the host, or assembly of the next generation of pathogen. In such embodiments, the invention features a method for treating, stabilizing, or preventing an infection in a subject (e.g., a vertebrate such as a mammal or human) or cell, tissue or organ derived from such a subject. These methods involve introducing into the subject or cell, tissue or organ derived therefrom an RNAi agent. The RNAi agent has substantial sequence identity and/or is substantially complementary to a region of a target gene in a pathogen (e.g., a virus, (e.g., a herpesvirus (e.g., herpes simplex, varicella-zoster virus, Epstein-Barr virus, cytomegalovirus (CMV)), hepatitis C, HIV, JC virus), bacteria or yeast), or in a cell, tissue or organ infected with a pathogen and specifically inhibits expression of the target gene. The pathogen can be an intracellular or extracellular pathogen, and the target gene can be, e.g., a gene of the pathogen that is necessary for replication and/or pathogenesis, or a gene encoding for a cellular receptor necessary for a cell, tissue or organ to be infected with the pathogen.

In a preferred aspect of the instant invention, a gene(s) encoding for a protein involved in apoptosis is targeted. Such genes include, e.g., bcl-2, p53, caspases, cytotoxic cytokines such as TNF-α or Fas ligand, and a number of other genes art-recognized as capable of mediating apoptosis. In certain embodiments of the invention, genes involved in cell growth can also be directedly targeted by the RNAi agents of the invention. Such genes include oncogenes (e.g., genes encoding for ABLI, BCLI, BCL2, BCL6, CBFA2, CBL, CSFIR, ERBA, ERBB, EBRB2, ETSI, ETSI, ETV6, FGR, FOS, FYN, HCR, HRAS, JUN, KRAS, LCK, LYN, MDM2, MLL, MYB, MYC, MYCLI, MYCN, NRAS, PIM I, PML, RET, SRC, TALI, TCL3, and YES), as well as genes encoding for tumor suppressor proteins (e.g., APC, BRCA1, BRCA2, MADH4, MCC, NF I, NF2, RB I, TP53, and WTI).

Alternatively, the gene targeted by the RNAi agent(s) of the instant invention can encode for a protein that may be a tumor-associated protein or an autoimmune disease-associated protein.

In exemplary embodiments, siRNA is delivered during or through the procurement of a pancreas (e.g., a donor pancreas) as well as during or through isolation of pancreatic islets from the pancreas. For delivery during the procurement of a pancreas, administration of the siRNA to the endocrine microvasculature is preferable. In certain embodiments, the invention features delivery of siRNA during or through the procurement of an organ (e.g., via administration via the vasculature of the pancreas) and during or through isolation of transplantable cells (e.g., islets) from the pancreas. siRNA-mediated gene therapy can be applied in several instances during procurement of the pancreas: 1) pre-procurement via intravenous perfusion in the deceased donor; 2) via organ perfusion prior to packaging the pancreas for transport; and/or 3) in pancreatic cell (e.g., islet cell) culture. The compositions and methods of the invention are particularly suited for altering the phenotype of pancreatic (e.g., islet) cells. In preferred applications, the compositions and methods of the invention are useful for altering genes such that islet engraftment, viability and/or function is enhanced, leading to improved outcomes in islet transplantation.

In certain embodiments, in vitro delivery (e.g., transfection) of siRNA (e.g., transfection) is such that at least a 25% reduction in target mRNA levels is observed. For example, siRNA is delivered at a concentration, dosage or according to a dosage regime (e.g., multiple doses over set time interval) such that the percent reduction in target mRNA levels is achieved. In other embodiments, in vitro delivery of siRNA is such that at least a 30-35% reduction in target mRNA levels is observed. In other embodiments, in vitro delivery of siRNA is such that at least a 35-40% reduction in target mRNA levels is observed. In other embodiments, in vitro delivery of siRNA is such that at least a 40-45% reduction in target mRNA levels is observed. In other embodiments, in vitro delivery of siRNA is such that at least a 45-50% reduction in target mRNA levels is observed. In yet other embodiments, in vivo delivery of siRNA is such that at least a 55%, 60%, 70% or 80% reduction in target mRNA levels is observed.

In certain embodiments, in vitro delivery (e.g., transfection) of siRNA (e.g., transfection) is such that at least 30% of the target cells incorporate the siRNA. In other embodiments, in vitro delivery (e.g., transfection) of siRNA (e.g., transfection) is such that at least 35% of the target cells incorporate the siRNA. In other embodiments, in vitro delivery (e.g., transfection) of siRNA (e.g., transfection) is such that at least 40% of the target cells incorporate the siRNA. In yet other embodiments, in vitro delivery (e.g., transfection) of siRNA (e.g., transfection) is such that at least 45%, 50%, 55% or 60% of the target cells incorporate the siRNA.

In exemplary embodiments, about 50-100 nM siRNA is delivered to or contacted with the target cells. In further embodiments, about 100-200 nM siRNA is delivered to or contacted with the target cells. In further embodiments, about 200-300 nM siRNA is delivered to or contacted with the target cells. In further embodiments, about 300-400 nM siRNA is delivered to or contacted with the target cells. In still further embodiments, greater than 500 nM siRNA is delivered to or contacted with the target cells.

IV. Methods of Introducing RNAs and RNAi Agents

Physical methods of introducing nucleic acids include injection of a solution containing the nucleic acid (e.g., RNAi agent), bombardment by particles covered by the nucleic acid (e.g., RNAi agent), soaking the cell, tissue, allograft or organism in a solution of the nucleic acid (e.g., RNAi agent), or electroporation of cell membranes or tissues/allografts in the presence of the nucleic acid (e.g., RNAi agent). Lipid-mediated carrier transport (e.g., liposome-mediated delivery) of an RNAi agent to a cell, tissue, allograft or organism is preferred in certain embodiments of the instant invention. A viral construct packaged into a viral particle may also accomplish both efficient introduction of an expression construct and/or RNAi agent into the cell, tissue, allograft or organism of the instant invention; and in the instance of a virally introduced expression construct, transcription of an RNAi agent may then occur. Other methods known in the art for introducing nucleic acids to cells may be used, such as chemical-mediated transport, such as calcium phosphate, and the like. Thus the nucleic acid (e.g., RNAi agent) may be introduced along with components that perform one or more of the following activities: enhance nucleic acid (e.g., RNAi agent) uptake by the cell, inhibit annealing of single strands, stabilize the single strands, or other-wise increase inhibition of the target gene.

The nucleic acid (e.g., RNAi agent) may be directly introduced into the cell (i.e., intracellularly), tissue, organ, allograft or organism; or introduced extracellularly into a cavity, interstitial space, into the circulation of an organism, introduced orally, or may be introduced by bathing a cell, tissue, organ, allograft or organism in a solution containing the nucleic acid (e.g., RNAi agent). The bile or biliary system, vascular or extravascular circulation, the blood or lymph system, and the cerebrospinal fluid are sites where the nucleic acid (e.g., RNAi agent) may be introduced.

In certain embodiments of the invention, an RNAi agent is exposed to a transplanted tissue (e.g. an organ) by perfusion. A tissue containing a vascular system is procured from a donor subject by methods adhering to clinical protocols, using cold storage in an appropriate solution (e.g., UW solution, also referred to as Belzer Organ Preservation solution). The isolated tissue may be tested to determine whether the RNAi agent can be perfused into the exocrine/endocrine tissues. "Catheters" are inserted into the tissue for input and output using the vascular system. Tubing of the "catheters" is connected to a peristaltic pump and the tissue is submerged in a chamber containing preservation solution (e.g. UW solution) at 4° C. Preservation solution, optionally containing a tracking dye (e.g., 5% trypan blue) then perfuses the tissue. The RNAi agent, optionally labeled with a fluorescent dye (e.g., Cy3), is also added to the perfusion media and allowed to circulate. While being perfused with the RNAi agent, the tissue may also be submitted to electric pulses via an electroporator to further diffuse the RNAi agent into the tissue and optimize delivery in situ. Following perfusion treatment, the tissue may be transplanted. Alternatively, if the tissue is to be used for research purposes, the tissue may be perfused for 24-48 hours, with the tissue then removed, fixed in buffered formalin, paraffin embedded, and sectioned. Fluorescence microscopy may then be used to identify the extent to which the RNAi agent has been delivered to the perfused tissue (in instances of pancreatic perfusion, e.g., labeled anti-insulin antibodies may be used to identify islet cells, with these islet cells additionally observed for delivery of the RNAi agent, in determining the extent to which the RNAi agent has been delivered to the exocrine and endocrine tissues).

Depending on the particular target gene and the dose of RNAi agent delivered, this process may provide partial or complete loss of function for the target gene. A reduction or loss of gene expression in at least 50%, 60%, 70%, 80%, 90%, 95% or 99% or more of targeted cells is exemplary. Inhibition of gene expression refers to the absence (or observable decrease) in the level of protein and/or mRNA product from a target gene. Specificity refers to the ability to inhibit the target gene without manifest effects on other genes of the cell. The consequences of inhibition can be confirmed by examination of the outward properties of the cell or organism (as presented below in the examples) or by biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS).

In certain embodiments, in vivo delivery of siRNA is such that at least a 20% reduction in target mRNA levels is observed. For example, siRNA is delivered at a concentration, dosage or according to a dosage regime (e.g., multiple doses over set time interval) such that the percent reduction in target mRNA levels is achieved. In other embodiments, in vivo delivery of siRNA is such that at least a 25-30% reduction in target mRNA levels is observed. In other embodiments, in vivo delivery of siRNA is such that at least a 30-35% reduction in target mRNA levels is observed. In yet other embodiments, in vivo delivery of siRNA is such that at least a 40%, 50%, 60% or 70% reduction in target mRNA levels is observed.

Depending on the assay, quantitation of the amount of gene expression allows one to determine a degree of inhibition which is greater than 10%, 33%, 50%, 90%, 95% or 99% as compared to a sample, e.g., a cell, tissue or organ not treated according to the present invention. Lower doses of injected material and longer times after administration of a RNAi agent may result in a controlled decrease in inhibition achieved. Quantitation of gene expression in a cell, tissue or organ may show similar amounts of inhibition at the level of accumulation of target mRNA or translation of target protein. As an example, the efficiency of inhibition may be determined by assessing the amount of gene product in the cell; mRNA may be detected with a hybridization probe having a nucleotide sequence outside the region used for the inhibitory double-stranded RNA, or translated polypeptide may be detected with an antibody raised against the polypeptide sequence of that region.

The RNAi agent may be introduced in an amount which allows delivery of at least one copy per cell. Higher doses (e.g., at least 5, 10, 100, 500 or 1000 copies per cell) of material may yield more effective inhibition; lower doses may also be useful for specific applications.

V. Delivery Vehicles for RNAi Agents

The RNAi agent(s) of the invention may also be admixed, encapsulated, conjugated or otherwise associated with other molecules, molecule structures or mixtures of compounds, as for example, liposomes, polymers, receptor targeted molecules, or other formulations, for assisting in uptake, distribution and/or absorption. The subject RNAi agent(s) can be provided in formulations also including penetration enhancers, carrier compounds and/or transfection agents.

The RNAi agents of the invention also encompass any pharmaceutically acceptable salts, esters or salts of such esters, or any other compound which, upon administration to a cell, tissue or organ, is capable of providing (directly or indirectly) the biologically active metabolite or residue thereof. Accordingly, for example, the disclosure is also drawn to RNAi agents and pharmaceutically acceptable salts of the siRNAs, pharmaceutically acceptable salts of such RNAi agents, and other bioequivalents.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,NI-dibenzylethylenediamine, chloroprocaine, choline, diethanolamine, dicyclohexylamine, eraylenediamine, N-methylglucamine, and procaine (see, for example, Berge et al., "Pharmaceutical Salts," *J. of Pharma Sci.* 1977, 66, 1-19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids.

For siRNA molecules, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalene disulfonic acid, polygalacturonic acid, and the like; and (d) salts formed from elemental anions such as chlorine, bromine, and iodine.

A. Supramolecular Complexes

The subject RNAi agent(s) of the instant invention may be formulated as part of a "supramolecular complex." To further illustrate, the RNAi agent can be contacted with at least one polymer to form a composite and then the polymer of the composite treated under conditions sufficient to form a supramolecular complex containing the RNAi agent and a multi-dimensional polymer network. The polymer molecule may be linear or branched. Accordingly, a group of two or more polymer molecules may be linear, branched, or a mixture of linear and branched polymers. The composite may be prepared by any suitable means known in the art. For example, the composite may be formed by simply contacting, mixing or dispersing the RNAi agent with a polymer. A composite may also be prepared by polymerizing monomers, which may be the same or different, capable of forming a linear or branched polymer in the presence of the expression agent. The composite may be further modified with at least one ligand, e.g., to direct cellular uptake of the expression agent or otherwise effect tissue or cellular distribution in vivo of the expression agent. The composite may take any suitable form and, preferably, is in the form of particles.

B. Liposome Formulations

In certain preferred embodiments, the invention provides composition including dsRNA or dsRNA-encoding plasmids that are encapsulated or otherwise associated with liposomes. Packaging and/or encapsulation of RNAi agents of the invention in liposomes may increase the efficiency of delivery of such agents. Merely to illustrate, dsRNA moieties or dsRNA-encoding plasmids can be condensed with a polycationic condensing agent, suspended in a low-ionic strength aqueous medium, and cationic liposomes formed of a cationic vesicle-forming lipid. The ratio of liposome lipids to plasmid can be adjusted achieving maximum transfection. That ratio, in nmole liposome lipid/μg plasmid, will often be greater than 5 but less than 25, and preferably greater than 8 but less than 18, and more preferably greater than 10 but less than 15 and most preferably between 12-14. Such complexes preferably have a substantially homogeneous size (i.e., ±20%, preferably ±10% or more preferably ±5% in size) of typically less than about 200 nm and preferably in the range of 50-200 nm.

Liposomes, as used herein, refer to lipid vesicles having an outer lipid shell, typically formed on one or more lipid bilayers, encapsulating an aqueous interior. In certain embodiments, the liposomes are cationic liposomes composed of between about 20-80 mole percent of a cationic vesicle-forming lipid, with the remainder neutral vesicle-forming lipids and/or other components. As used herein, "vesicle-forming lipid" refers to any amphipathic lipid having hydrophobic and polar head group moieties and which by itself can form spontaneously into bilayer vesicles in water, as exemplified by phospholipids. A preferred vesicle-forming lipid is a diacyl-chain lipid, such as a phospholipid, whose acyl chains are typically between about 14-22 carbon atoms in length, and have varying degrees of unsaturation.

A cationic vesicle-forming lipid is one whose polar head group with a net positive charge, at the operational pH, e.g., pH 4-9. Typical examples include phospholipids, such as phosphatidylethanolamine, whose polar head groups are derivatized with a positive moiety, e.g., lysine, as illustrated, for example, for the lipid DOPE derivatized with L-lysine (LYS-DOPE) (Guo, et al., 1993). Also included in this class are the glycolipids, such as cerebrosides and gangliosides having a cationic polar head-group.

Another cationic vesicle-forming lipid which may be employed is cholesterol amine and related cationic sterols. Exemplary cationic lipids include 1,2-diolelyloxy-3-(trimethylanuno) propane (DOTAP); N-[1-(2,3,-ditetradecyloxy)propyl]-N,N-dimethyl-N-hydroxyethylammonium bromide (DMRIE); N-[1-(2,3,-dioleyloxy)propyl]-N,N-dimethyl-N-hydroxy ethylammonium bromide (DORIE); N-[1-(2,3-dioleyloxy)propyl]-N,N,N-trimethylammonium chloride (DOTMA); 3β [N—(N',N'-dimethylaminoethane) carbamoyl] cholesterol (DC-Choi); and dimethyldioctadecylammonium (DDAB).

The remainder of the liposomes are formed of neutral vesicle-forming lipids, meaning vesicle forming lipids which have no net charge or which may include a small percentage of lipids having a negative charge in the polar head group. Included in this class of lipids are the phospholipids, such as phosphatidylcholine (PC), phosphatidyl ethanolamine (PE), phosphatidylinositol (PI), and sphingomyelin (SM), and cholesterol, cholesterol derivatives, and other uncharged sterols.

The above-described lipids can be obtained commercially, or prepared according to published methods. Other lipids that can be included in the invention are glycolipids, such as cerebrosides and gangliosides.

The RNAi agent-liposome complex employed in certain embodiments of the instant invention may include liposomes having a surface coating of hydrophilic polymer chains, effective to extend the blood circulation time of the plasmid/liposome complexes. Suitable hydrophilic polymers include cyclodextrin (CD), polyethylene glycol (PEG), polylactic acid, polyglycolic acid, polyvinyl-pyrrolid-one, polymethyloxazoline, polyethyloxazoline, polyhydroxypropyl methacrylamide, polymethacrylamide, polydimethylacrylamide, and derivatized celluloses, such as hydroxymethylcellulose or hydroxyethyl-cellulose. A preferred hydrophilic polymer chain is polyethyleneglycol (PEG), preferably as a PEG chain having a molecular weight between 500-10,000 daltons, more preferably between 1,000-5,000 daltons. The hydrophilic polymer may have solubility in water and in a non-aqueous solvent, such as chloroform.

The coating is preferably prepared by including in the vesicle-forming lipids a phospholipid or other diacyl-chain lipid, derivatized at its head group with the polymer chain. Exemplary methods of preparing such lipids, and forming polymer coated liposomes therewith, have been described in U.S. Pat. Nos. 5,013,556, and 5,395,619, which are incorporated herein by reference.

It will be appreciated that the hydrophilic polymer can be stably coupled to the lipid, or coupled through an unstable linkage which allows the polymer-coated plasmid-liposome complexes to shed or "release" the hydrophilic polymer coating during circulation in the bloodstream or after localization at a target site. Attachment of hydrophilic polymers, in particular polyethyleneglycol (PEG), to vesicle-forming lipids through a bond effective to release the polymer chains in response to a stimulus have been described, for example in WO 98/16202, WO 98/16201, which are hereby incorporated by reference, and by Kirpotin, D. et a. (*FEBS Lett.* 1996 388, 115-118).

The releasable linkage, in one embodiment, is a chemically releasable linkage which is cleaved by administration of a suitable releasing agent or is cleaved under selective physiological conditions, such as in the presence of enzymes or reducing agents. For example, ester and peptide linkages are cleaved by esterase or peptidase enzymes. Disulfide linkages are cleaved by administration of a reducing agent, such as glutathione or ascorbate, or by a reducing agent present in vivo, such as cysteine, which is present in plasma and intracellularly.

Other releasable linkages include pH sensitive bonds and bonds which are cleaved upon exposure to glucose, light or heat. By way of an example, the hydrophilic polymer chains can be attached to the liposome by a pH sensitive bond, and the plasmid-liposome complexes are targeted to a site having a pH effective to cleave the bond and release the hydrophilic chains, such as a tumor region. Exemplary pH sensitive bonds include acyloxyalkyl-ether, acetal and ketal bonds.

Another example is where the cleavable bond is a disulfide bond, broadly intended herein to refer to sulfur-containing bonds. Sulfur-containing bonds can be synthesized to achieve a selected degree of lability and include disulfide bonds, mixed sulfide-sulfone bonds and sulfide-sulfoxide bonds. Of the three bonds, the disulfide bond is least susceptible to thiolysis and the sulfide-sulfoxide bond is most susceptible.

Such releasable bonds are useful to tailor the rate of release of the hydrophilic polymer segment from the liposome complexes. For example, a very labile disulfide bond can be used for targeting to blood cells, isolated islet cells or endothelial cells, since these cells are readily accessible and a shorter liposome blood circulation or delivery lifetime is sufficient. At the other extreme, a long-lasting or hearty disulfide bond can be used when the target is a whole organ or other tissue where a longer liposome blood circulation or delivery lifetime is generally needed for the complexes to reach the desired target.

The releasable bond attaching the hydrophilic polymer chains to the liposome is cleaved in vivo typically as a result of change in environment, such as when the liposomes reach a specific site with a slightly lower pH, such as a region of tumor tissue, or a site with reducing conditions, such as a hypoxic tumor. Reducing conditions in vivo can also be effected by administration of a reducing agent, such as ascorbate, cysteine or glutathione. The cleavable bond may also be broken in response to an external stimulus, such as light or heat.

Additionally, the liposome complexes may include an affinity moiety or targeting ligand effective to bind specifically to target cells at which the therapy is aimed. Such moieties can be attached to the surface of the liposome or to the distal ends of hydrophilic polymer chains. Exemplary moieties include antibodies, ligands for specific binding to target cell surface receptors and the like, as described, for example, in PCT application Nos. WO US94/03103, WO 98/16202 and WO 98/16201. The moiety can also be a hydrophobic segment to facilitate fusion of the complex with a target cell.

Polycationic condensing agents used to condense the dsRNA and dsRNA-encoding plasmids can be multiply charged cationic polymers, and are preferably biopolymers such as such as spermidine, spermine, polylysine, protamine, total histone, specific histone fractions such as H1, H2, H3, H4, and other polycationic polypeptides, but may also include biocompatible polymers, such as polymyxin B. It will be appreciated that these polycationic condensing agents can be used in free base or salt forms, for example, protamine sulfate and polylysine hydrobromide. The polycationic condensing agent may be a histone, which, as referred to herein, includes total histone or specific histone fractions.

The hydrophobic segment in the polymer-lipid conjugate may be a hydrophobic polypeptide sequence. Preferably, the polypeptide sequence consists of about 5-80, more preferably 10-50, most preferably 20-30, non-polar and/or aliphatic/aromatic amino acid residues. These sequences are active in triggering fusion of certain enveloped viruses with host cells and include Parainfluenza viruses, such as Sendai, Simian Virus-5 (SV5), measles virus, Newcastle Disease Virus (NDV) and Respiratory Syncytial Virus (RSV)— Other examples include human retroviruses, such as Human Immunodiffiency Virus-1 (HTV-1), the causative agent of AIDS, which infects cells by fusion of the virus envelope with the plasma membrane of the host cell. Fusion occurs at physiological (i.e., neutral) pH and is followed by injection of the viral genetic material (nucleocapsid) into the cytoplasmic compartment of the host cell.

C. Ligand-Directed Formulations

The supramolecular complexes and liposomes of the subject invention can be associated with one or more ligands effective to bind to specific cell surface proteins or matrix on the target cell, thereby facilitating sequestration of the complex to target cells, and in some instances, enhancing uptake of the RNAi agent by the cell. Merely to illustrate, examples of ligands suitable for use in targeting the supramolecular complexes and liposomes of the present invention to specific cell types are listed in Table 1 below.

TABLE 1

Sample ligands of potential use in targeting liposomes and other RNAi agent delivery complexes

| Ligand | Receptor | Cell type |
| --- | --- | --- |
| folate | folate receptor | epithelial carcinomas, bone marrow stem cells |
| water soluble vitamins | vitamin receptor | various cells |
| pyridoxyl phosphate | CD4 | CD4$^+$ lymphocytes |
| apolipoproteins | LDL | Liver hepatocytes, vascular endothelial cells |
| insulin | insulin receptor | |
| transferrin | transferrin receptor | endothelial cells |
| galactose | asialoglycoprotein receptor | liver hepatocytes |
| sialyl-Lewis$_x$ | E, P selectin | activated endothelial cells |
| Mac-1 | L selectin | neutrophils, leukocytes |
| VEGF | Flk-1,2 | tumor epithelial cells |
| basic FGF | FGF receptor | tumor epithelial cells |
| EGF | EGF receptor | epithelial cells |
| VCAM-1 | a$_4$b$_1$ integrin | vascular endothelial cells |
| ICAM-1 | a$_L$b$_2$ integrin | vascular endothelial cells |
| PECAM-1/CD31 | a$_v$b$_3$ integrin | vascular endothelial cells, activated platelets |
| osteopontin | a$_v$b$_1$ integrin a$_v$b$_5$ integrin | endothelial cells and smooth muscle cells in atherosclerotic plaques |
| RGD sequences | a$_v$b$_3$ integrin | tumor endothelial cells, vascular smooth muscle cells |
| HIV GP 120/41 or GP120 | CD4 | CD4$^+$ lymphocytes |

VI. Methods of Treatment

The present invention provides for both prophylactic and therapeutic methods of treating a subject at risk of (or susceptible to) a disorder or having a disorder associated with aberrant or unwanted target gene expression or activity. "Treatment", or "treating" as used herein, is defined as the application or administration of a therapeutic agent (e.g., an RNAi agent, vector or transgene encoding same) to a patient, or application or administration of a therapeutic agent to an isolated tissue or cell line from a patient, who has a disease or disorder, a symptom of disease or disorder or a predisposition toward a disease or disorder, with the purpose to cure, heal, alleviate, relieve, alter, remedy, ameliorate, improve or affect the disease or disorder, the symptoms of the disease or disorder, or the predisposition toward disease.

With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with either the target gene molecules of the present invention or target gene modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

In one aspect, the invention provides a method for preventing in a subject, tissue rejection, disease or other deleterious transplantation outcome which is caused or contributed to by aberrant or unwanted target gene expression or activity, by administering to the subject a therapeutic agent (e.g., an RNAi agent, e.g., an RNAi modulatory agent, or vector or transgene encoding same). Subjects at risk for such deleterious transplantation outcome(s) can be identified by, for example, any or a combination of diagnostic or prognostic assays as described herein. Prophylactic treatment can occur prior to the manifestation of symptoms characteristic of the target gene aberrancy, such that a disease, disorder, or outcome is prevented or, alternatively, delayed in its progression.

Another aspect of the invention pertains to methods for treating a subject having or experiencing tissue rejection, disease or other deleterious transplantation outcome which is caused or contributed to by aberrant or unwanted target gene expression or activity. Accordingly, in an exemplary embodiment, the modulatory method of the invention involves contacting a cell, tissue or organ capable of expressing target gene with a therapeutic agent (e.g., an RNAi agent, e.g., an RNAi modulatory agent, or vector or transgene encoding same) that is specific for the target gene or protein such that expression or one or more of the activities of target protein is modulated. These modulatory methods can be performed in vitro (e.g., by culturing the cell with the agent) or, alternatively, in vivo (e.g., by administering the agent to a subject). As such, the present invention provides methods of treating an individual afflicted with a disease or disorder (e.g., transplant rejection) characterized by aberrant or unwanted expression or activity of a target gene polypeptide or nucleic acid molecule. Inhibition of target gene activity is desirable in situations in which target gene is abnormally unregulated and/or in which decreased target gene activity is likely to have a beneficial effect.

Therapeutic methods and compositions can be tested in an appropriate animal model. For example, a modulatory agent or RNAi agent (or expression vector or transgene encoding same) as described herein can be used in an animal model to determine the efficacy, toxicity, or side effects of treatment with said agent. Alternatively, a therapeutic agent can be used in an animal model to determine the mechanism of action of such an agent.

While the methods of the instant invention primarily involve treatment of transplanted animal tissues with RNAi agents, such RNAi agents may also be administered to transplanted plant tissues. Administration of an RNAi agent to a transplanted plant tissue may be performed through, e.g., injection of the RNAi agent to a plant or plant tissue in a manner equivalent to those methods of the instant invention related to perfusion of animal tissues. Compositions designed to aid administration of agents to plants are described, for example, in WO 03/020024, the contents of which are incorporated herein by reference.

VII. Pharmaceutical Compositions

The invention pertains to uses of the above-described agents for therapeutic treatments as described infra. Accordingly, the modulators or agents of the present invention can be incorporated into pharmaceutical compositions suitable for administration. Such compositions typically comprise the RNAi agent and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, intraperitoneal, intramuscular, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

In certain embodiments of the instant invention, RNAi agents are prepared with carriers that will protect the compound against rapid elimination from the body, such as a controlled release formulation, including implants and microencapsulated delivery systems. The RNAi agents of the invention may also be prepared with carriers that will enhance delivery and/or targeting of the agents to an appropriate cell, tissue or organ. Such carriers and delivery vehicles are art-recognized, with certain preferred delivery modes for the instant invention detailed above.

The pharmaceutical compositions can be included in a container, pack, or dispenser together with instructions for administration.

The invention is further described in the Examples below which describe the successful treatment of commonly transplanted cells and whole organs with RNAi agents. The following examples should not be construed as limiting. The

EXAMPLES

Example I: Effective Ex Vivo Treatment of Isolated Islet Cells with siRNA

The efficacy of administration of siRNA to islet cells in culture was examined. Islet cells were isolated from C57BL/6 mice by methods previously described (Ricordi, C and Rastellini, C. Automation in Islet Isolation. In: Ricordi, C, ed. Methods in Cell Transplantation. Austin, Tx, USA: RG Landes Co. 1995; Salvalaggio PRO et al. *Transplantation*. 2002, 74:877-900), and these cells were employed to assess the ability of siRNA molecules directed against a green fluorescent protein (GFP) to downregulate production of GFP expressed from an exogenously introduced adenoviral vector (adeno-GFP). Successful cellular incorporation of the anti-GFP siRNA was anticipated to diminish green fluorescence of cultured islet cells. Three groups were used: 1) a negative control, wherein cells were administered no siRNA, 2) a non-specific siRNA control, and 3) siRNA directed to inhibit GFP (anti-GFP siRNA). Those islet cells transfected with siRNA were transfected for 24 hours, allowing enough time for absorbed siRNA to prime RISC prior to subsequent infection of the islet cells with adeno-GFP for 24 hours. Reduced levels of green fluorescence were observed for islet cells that were treated with anti-GFP siRNA, as compared to fluorescence observed for those cells either left untreated or treated with a non-specific siRNA (FIG. 1). An siRNA dose of 100 nM using a Lipofectamine 2000 (Invitrogen) transfection kit was observed to effect introduction of the siRNA into 20 islet cells per culture well. Anti-GFP siRNA was therefore shown to effectively reduce GFP production in cultured islet cells.

Example II: Effective Perfusion of Whole Pancreas In Situ with siRNA

Figure 2:
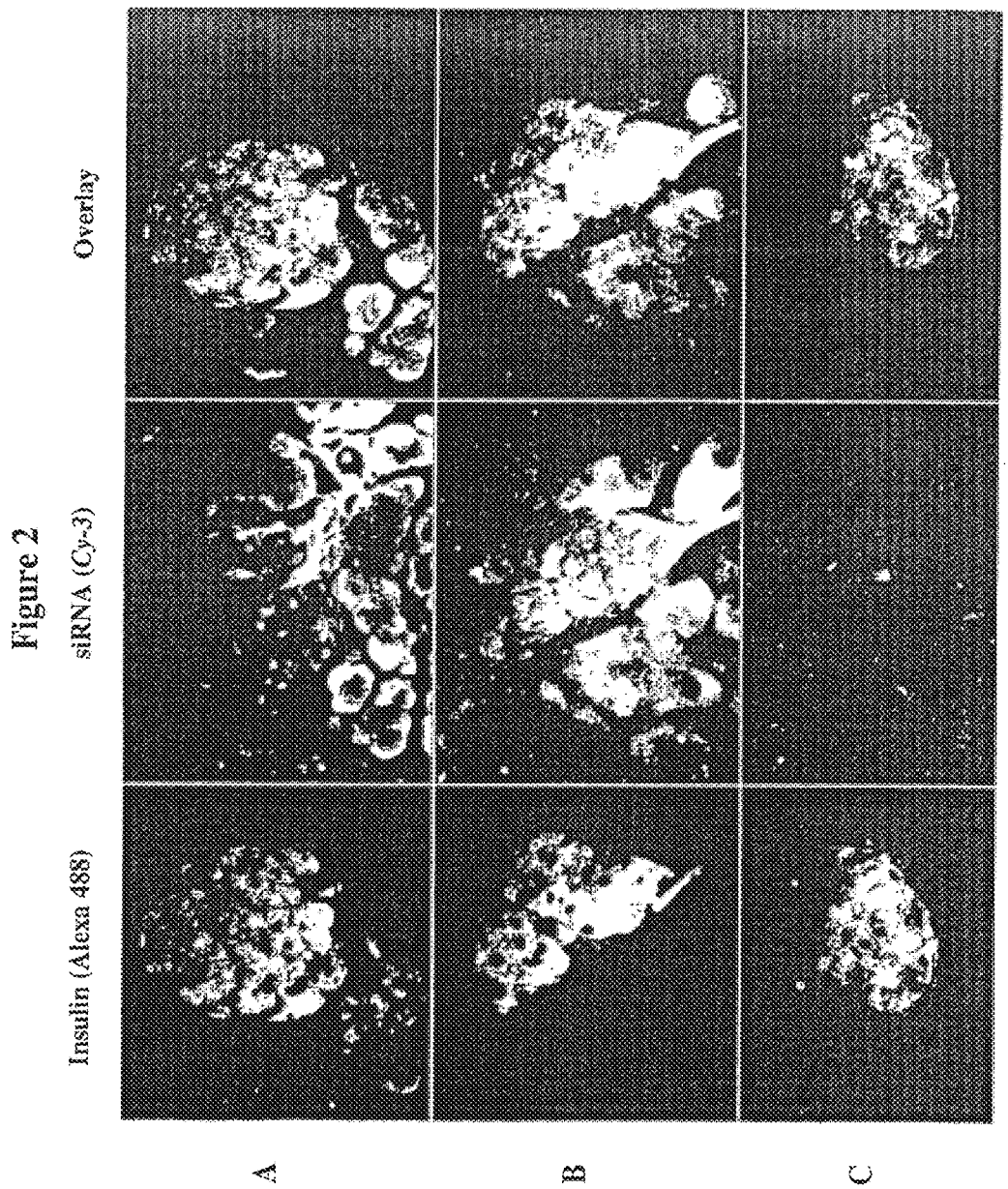
FIG. 2 depicts results showing the success of direct organ perfusion (specifically, perfusion of pancreatic islet cells in situ via portal vein administration) with siRNA (red fluorescence, Cy-3 labeled). Panel A shows the effect of administration of "naked" siRNA, while cells in panel B were administered siRNA packaged into liposomes using Lipofectamine 2000. Cells in panel C were left untreated.
Figure 3:
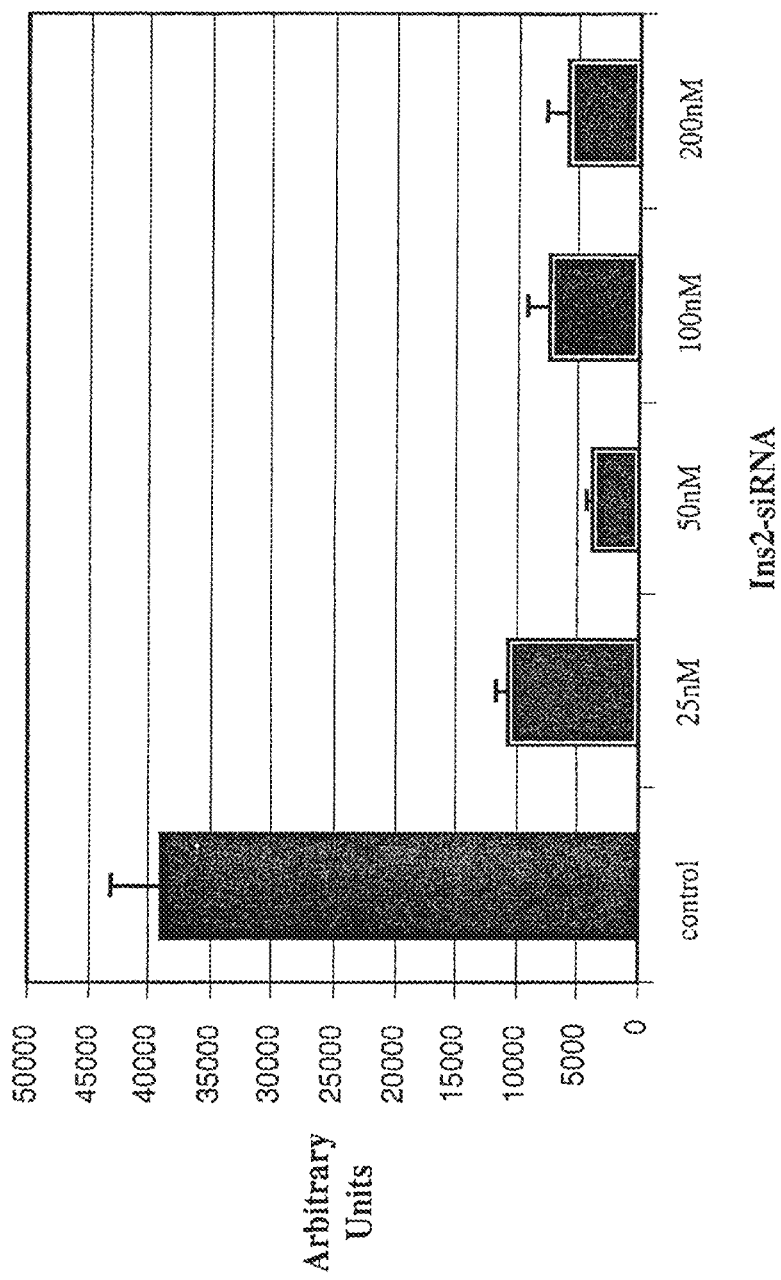
FIG. 3 graphically depicts inhibition of native insulin production observed in islet cells isolated from whole pancreas following perfusion with anti-Insulin 2 siRNA. Assays were performed in triplicate, with positive standard deviations indicated.

Given the efficacy observed for siRNA administration to cultured islet cells, studies were performed to examine the effect of siRNA perfusion to whole pancreas. Initial studies were conducted to test surgical procedures for siRNA injection into pancreas of BALB/c mice. siRNA was either injected as "naked" molecules or packaged into liposomes using Lipofectamine 2000 (Invitrogen). The control siRNA used was labeled with the red-fluorophore, Cy-3, to track the siRNA location in the tissue. 1 c.c. containing 2 µg siRNA/liposomes in UW (University of Wisconsin, Belzer Organ Preservation) solution+6% trypan blue was injected via retrograde portal vein. siRNA injections with naked siRNA resulted in poor diffusion into the tissue. After injections, pancreata were removed and stored at 4° C. for 20 hours. Organs were fixed in buffered formalin, paraffin embedded, and sections were stained for insulin with immunofluorescence. The fluorescent images of insulin-stained pancreatic islets from siRNA-treated versus untreated mice pancreata are shown in FIG. 2. Both siRNA-treated sections showed substantial siRNA uptake by the islets as observed in the Cy-3 red fluorescent images, when compared to the background auto-fluorescence in the untreated control section (compare FIG. 2, center panels A and B with center panel C). Thus, successful direct organ perfusion with siRNA was demonstrated.

Example III: Suppressed Insulin Production Via Whole Pancreas siRNA Perfusion Whole mouse pancreas was perfused (by the methods of the preceding Example) with anti-Insulin 2 siRNA (Ambion pre-designed siRNA ID #62419). Such experiments demonstrated the efficacy with which perfused RNAi agents were capable of suppressing production of a native transcript in a whole tissue. Following perfusion of whole pancreas with anti-Insulin 2 siRNA, islet cells were isolated using standard islet preparation procedures as described, e.g., in Jonas, J. C., et al. (*Diabetes* 1998 47, 1266-73). Isolated islet cells were then transferred to wells for performance of real-time RT-PCR. Each well contained 200 islet cells. Real-time RT-PCR was performed in triplicate on lysed cells using a FAM-labeled Insulin-specific TaqMan probe (Roche Molecular Systems, Inc.), with FAM fluorescence detected by an ABI 5700 machine. Islet cells isolated from whole mouse pancreas that had been perfused with varying concentrations (25 nM, 50 nM, 100 nM, and 200 nM) of anti-Insulin 2 siRNA exhibited dramatic reductions in insulin production, when compared to control islet cells isolated from pancreas that had been perfused with a control (anti-luciferase) siRNA. Whole tissue-perfused RNAi agents were thus shown to dramatically reduce production of a native transcript.

Example IV: Perfusion of Transplantable Tissues

Demonstration of successful direct organ perfusion with siRNA enables the improvement of transplantation outcomes through contacting tissues with siRNA prior to or during transplantation. siRNA may be directly perfused during or shortly after the organ procurement process. As organs are dissected and isolated on their vascular pedicles, organ-specific siRNA can be delivered into the tissue via any afferent (or efferent retrograde) vessel.

Example V: Effective Delivery and Function of siRNA in Isolated Islets In Vitro Pancreatic islets were isolated from BALB/c mice, and 200 islets were placed into wells of a 48 well plate in 1 ml 10% FBS CMRL 1066 supplemented Cellgro media (Mediatech, Inc., Herndon, Va.). Samples were divided into 3 groups: (a) untreated control, (b) Ins2-siRNA transfected, and (c) Luc-siRNA transfected islets as a non-specific siRNA control. For in vitro delivery, the siRNA were packaged using Lipofectamine 2000 (Invitrogen, Carlsbad, Calif.) at a DNA-to-liposome (µg/µl) ratio of 1:3, following the manufacturer's recommendations in a delivery volume of 100 µl. Dose titrations of 0, 50, 100, 200, and 400 nM final concentration were used for the experimental and non-specific control siRNA. Samples were transfected and incubated at 37° C., 5% $CO_2$ for 48 hours followed by RNA isolation for cDNA synthesis and quantitative-RT-PCR. To determine to what extent siRNA could transfect pancreatic islets, fluorescent conjugated siRNAs were used following the same protocol used in the dose titration. A Cy-3-labeled Luc-siRNA was used to qualitatively assess the incorporation of siRNA utilizing fluorescent microscopy and FACS was used to quantitate siRNA transfection efficiency using a FITC-labeled Luc-siRNA.

Figure 4:
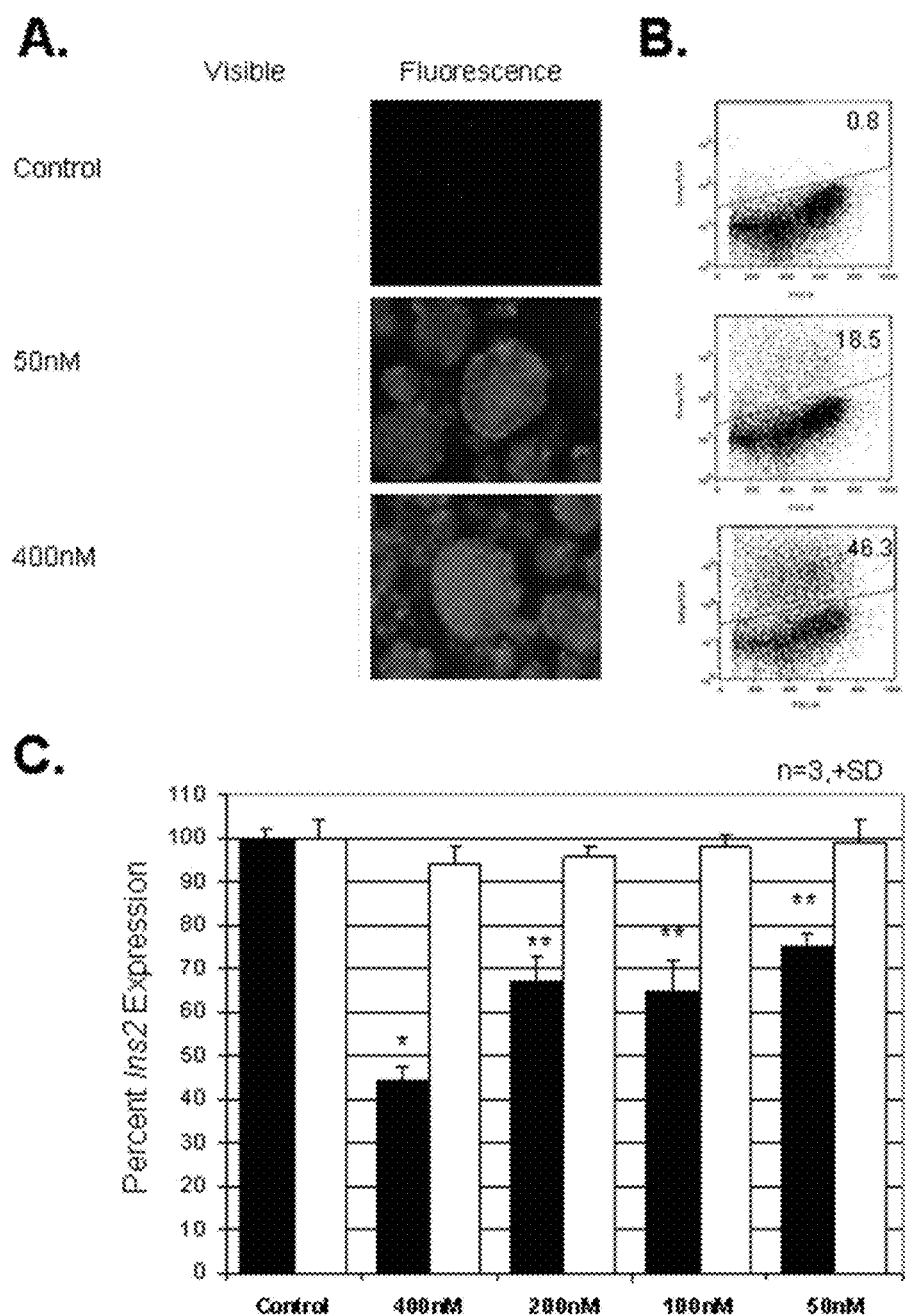
FIG. 4 (A,B,C) shows the efficacy of siRNA delivery and function in isolated islets in vitro.

FIG. 4A demonstrates that primary islets were transfected with the Cy-3-siRNA and clearly shows that siRNA can be introduced into islets in culture. FACS data in FIG. 4B, revealed that more than 45% of islet cells incorporated the FITC-labeled siRNA (400 nM siRNA concentration). FIG. 4C depicts the normalized real-time PCR data comparing the Ins2 expression levels of samples from the three groups and demonstrates that all concentrations of Ins2-siRNA used were able to significantly reduce Ins2 transcript levels in pancreatic islets, in vitro. In sum, it was shown that Ins2-siRNA can functionally inhibit Ins2 gene expression in pancreatic islets when delivered in vitro by transfection.

Example VI: Effective Delivery and Function of siRNA in Pancreatic Islets In Vivo by Tail Vein Injection For hydrodynamic injections synthetic siRNA, 100 µg in 0.8 ml PBS, was rapidly injected into one of the side tail veins. The siRNA was delivered 'naked', without liposomal transfection reagents. To examine in vivo siRNA cellular uptake and transfection efficiency in pancreatic islets, siRNA-treated and PBS treated control mice (n=3) were used. One hundred µg of Cy-3-Luc-siRNA, a red fluorescent fluorophore, was administered to 3 mice of the siRNA-treated group. Islets were isolated and purified four hours later from all mice in both groups and were cultured for 16 hours using 48 well plates in 1 ml 10% FBS CMRL 1066 supplemented Cellgro media, followed by imaging with fluorescent microscopy. Following the same protocol using a FITC-Luc-siRNA, isolated islets were treated with 0.25% trypsin/EDTA then prepared for FACS analysis to quantitatively determine the percentage of islet cells that incorporated FITC-Luc-siRNA. To assess Ins2-siRNA function in pancreatic islets, mice were divided into 3 groups (n=3/group) as follows: group 1, the PBS-treated control; group 2, received Ins2-siRNA; group 3, was a non-specific siRNA control receiving Luc-siRNA. Four hours after mice received tail vein injections their islets were isolated and cultured for 16 hours (37° C., 5% $CO_2$) followed by total RNA isolation for cDNA synthesis and quantitative RT-PCR for measuring the Ins2 gene transcript levels. All experiments were carried out in triplicate.

Figure 5:
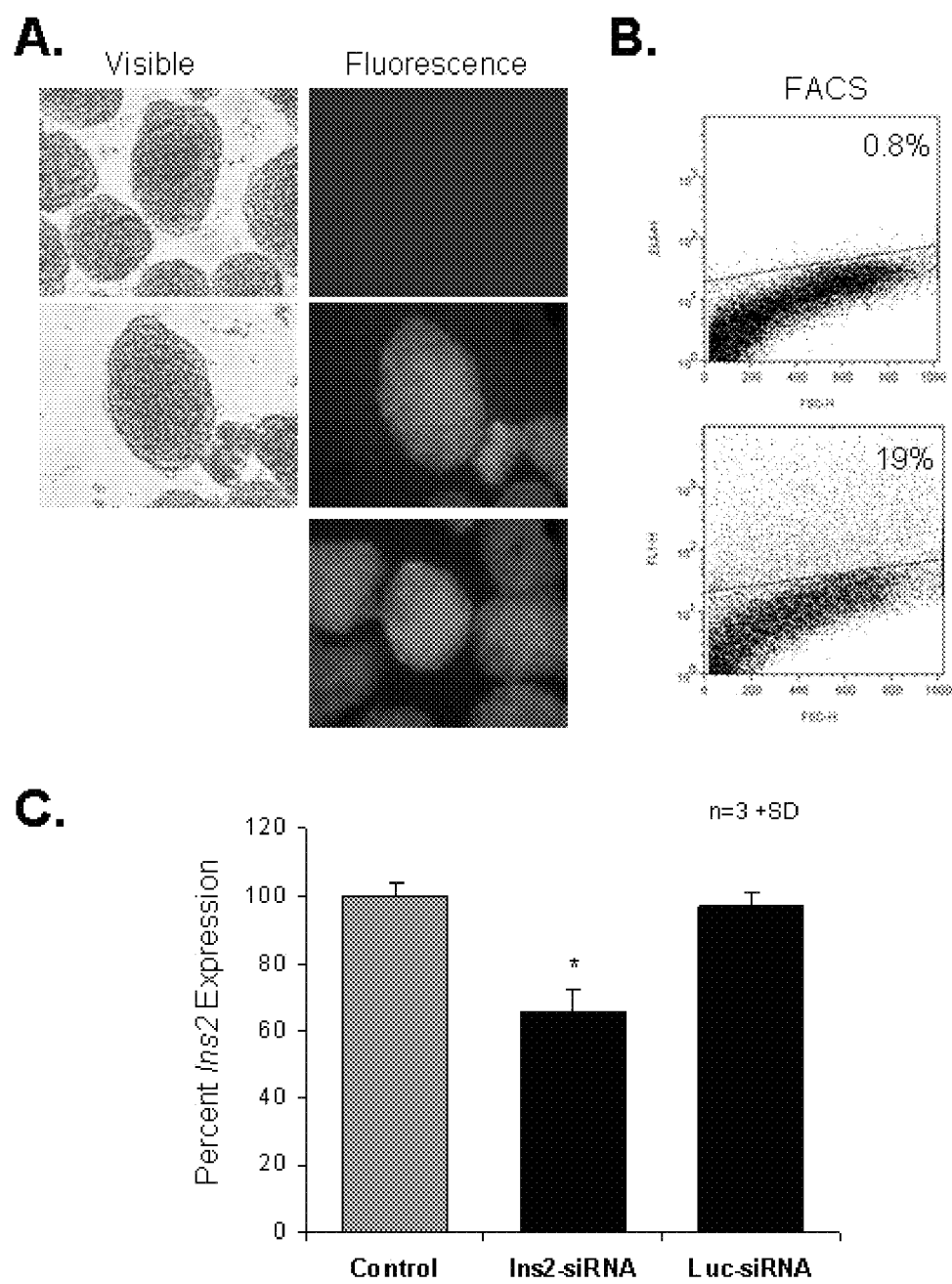
FIG. 5. (A,B,C) depicts the efficacy of delivery and function of siRNA in vivo.

Fluorescent microscope images (FIG. 5A) revealed all diffusely red islets from the mice that received Cy-3-siRNA while no red fluorescence was observed from the control treated islets. These images showed that siRNA was able to reach the islets by way of the pancreatic endocrine microvasculature, and also showed that in vivo delivery of siRNA to pancreatic islets was also achievable. The measurement of siRNA transfection efficiency using FITC-Luc (FIG. 5B) revealed that 19% of islet cells had incorporated siRNA. Assessment of Ins2-siRNA function in vivo is shown in FIG. 5C as a bar graph of the quantitative RT-PCR normalized data. The Ins2 expression level from the treated control sample was set at 100%. The average value from Ins2-siRNA treated samples showed a significant reduction in expression compared to untreated control samples (65.5% vs. 34.5%; P<0.05). The siRNA effect was gene specific as the non-specific siRNA controls had the same Ins2 expression levels as PBS treated control. Thus, it was shown that Ins2-siRNA can functionally inhibit Ins2 gene expression in pancreatic islets when delivered by intravenous injection in vivo.

Example VII: Exemplary siRNA Formulations

The methods of the present invention can be applied using any art-recognized siRNA. Exemplary siRNA molecules, including two newly-derived siRNA molecules that target the viral DNA polymerase of human cytomegalovirus (HCMV), that can be used in practicing the present invention are shown in Table 2.

TABLE 2

Examples of siRNA Sequences for Targeting of Sample Candidate Host and Viral Genes (SEQ ID NOS 1-11, respectively, in order of appearance)

| Human Gene Target | siRNA Sequence | Reference |
|---|---|---|
| PML-4 | 5' AACGACAGCCCAGAAGAGGAA | JBC 279: 1838-44, 2004 |
| c-myc | 5' CAGAAAUGUCCUGCAAUUU | Breast Cancer Res. 7: 220-228, 2005 |
| Bcl-2 | 5' GUGAAGUCAACAUGCCUGC-dTdT | Clin Cancer Res. 10: 7721-6, 2005 |
| BAX | 5' UAUGGAGCUGCAGAGGAUGdTdT | Cancer Res. 65: 309-16, 2005 |
| BID | 5' GAAGACAUCAUCCGGAAUA-dTdT | JBC 279: 35047-52, 2004 |
| Caspase 3 | 5' UGGAUUAUCCUGAGAUGGGdTdT | Blood 103: 4310-6, 2004 |
| Caspase 8 | 5' CUACCAGAAAGGUAUACCUdTdT | Nature 419: 395-9, 2002 |
| Apaf-1 | 5' GUGAACCAGGAUGGGUCACCA | Science 297: 1352-54, 2002 |
| H-ras | 5' GGGCAAGAGUGCGCUGACCAUC | Oncogene 22: 5694-5701, 2003 |

| Viral (HCMV) Gene Target | siRNA Sequence | Reference |
|---|---|---|
| UL54 | 5' CUGCUCAACAAGUGGGUUU-dTdT | New |
| UL54 | 5' GUUUUCAGAGCCGUGUUUU-dTdT | New |

Thus, Table 2 is exemplary of siRNAs that can be used in the methods of the instant invention; and one of skill in the art will recognize that the methods of the invention can be practiced with any number of siRNA molecules exerting preventive and/or therapeutic effects in transplantation.

The use of gene therapy in transplant research has mainly focused on a gain of function strategy where the gene of interest is expressed using a viral vector for delivery. Animal studies have explored attempts to reduce graft rejection by over-expressing genes whose products will interfere in the co-stimulatory cascade preventing donor T cell activation. Genes used have encoded the fusion proteins CTLA-4Ig and CD40-Ig, expressed from adenovirus (Takehara, M et al. *Human Gene Ther.* 2001 12: 415-426; Guillot, C et al. *J Immunol.* 2002 168: 1600-1609). Induction of molecular chimerism by expression of virally transduced allogeneic donor-type MHC class I genes in bone marrow has had limited success leading to the prolonged survival of cardiac and skin allografts (Tian, C et al. *Front Biosci.* 2002 7: 1331-1337; Bagley, J et al. *Blood.* 2002 99: 4394-4399). However, although viral vectors are promising in basic science and pre-clinical models, safety concerns have arisen due to fatalities reported from clinical gene therapy trials using viral vectors (Thomas, C E et al. *Nature Rev Genetics* 2003 4: 346-358) and their use in transplant is potentially dangerous because of recipient immunosuppression. In contrast, RNAi offers a non-viral method for gene modulation and thus can potentially eliminate the complications associated with viral vectors, while the utilization of siRNA adopts a strategy of loss of gene function.

RNA interference of gene expression is an attractive method for altering a phenotype of transplantable tissue. For example, manipulation of gene expression levels at the time of islet procurement and isolation can serve to enhance the survival and function of the islet cell mass and could then theoretically result in greater clinical success in islet transplantation. In the present examples, it is demonstrated that Ins2-siRNA can functionally inhibit Ins2 gene expression in pancreatic islets whether delivered in vitro by transfection or by intravenous injection in vivo. Quantitative RT-PCR confirms the functional transfection of siRNA for an organ-specific gene, thus evidencing proof-of-concept.

It was hypothesized that isolated intact islets could be sufficiently transfected with siRNA which would significantly reduce target gene expression. The FACS and quantitative RT-PCR data (FIG. 4) validated this hypothesis. This reduction was specific in its effect, as control siRNA did not significantly reduce Ins2 beyond background levels. The functional data demonstrates that siRNA can silence genes in primary whole islets, in vitro, also both the fluorescent images for the siRNA dose titration and the more quantitative FACS data help document how much siRNA was incorporated into islet cells. It is postulated that cationic liposomal formulations may increases siRNA transfection efficiency in vitro. The transfection efficiency of 46% with Lipofectamine 2000 in primary islets indicates that siRNA may penetrate beyond the periphery into a larger percentage of an islet cell mass than previously thought. The above examples demonstrate that transfection efficiency is preserved through the procurement of an organ and isolation of potentially transplantable cells (islets). These data demonstrate both the in vivo delivery and functional inhibition of target gene expression by siRNA targeted to an endogenous gene in pancreatic islets. Both the fluorescent tagged siRNA experiments showed incorporation of siRNA into pancreatic islets after in vivo administration. The FACS data showed that 19% of the islet cells in suspension had incorporated the synthetic siRNA molecules, this low efficiency may be due to the physical transport of siRNA across the cell membrane, as well as, a dosage effect. The real-time PCR data revealed that tail vein administration of 100 µg Ins2-siRNA significantly ($P<0.05$) reduced the Ins2 gene transcript levels. It has been shown by fluorescent imaging that in vivo delivery of 'naked' siRNA to pancreatic islets is feasible with intravenous tail vein injection without such high pressures as to damage vessels or harm the animal. Microvascular studies of the dense pancreatic islet capillary network describe a physical route existing through the porous capillary lumen basement membrane and fenestrated endothelium through which siRNA molecules may contact individual islet cells, and especially β-cells. These data support the observation that transfection of the siRNA in vivo does not require a liposomal based transfection reagent, indicating that naked siRNA may have an endocytic pathway of entry into cells. Interestingly, it has been demonstrated that intravenous administration of siRNA minimally induces, if any, an IFN response in mice (Heidel, J D et al. *Nat Biotechnol.* 2004 22: 1579-1582). It is proposed that the ability to deliver siRNA to the donor pancreatic islets prior to procurement and isolation may allow the gene silencing process to initiate and have a greater effect on phenotypic change.

What is claimed:

1. A method of inhibiting apoptosis-induced ischemic injury of a transplanted allograft organ, comprising perfusing the vasculature of the allograft organ with an RNAi agent capable of downmodulating ischemia-induced apoptosis, wherein the RNAi agent comprises a sense strand and an anti-sense strand, wherein the anti-sense strand is sufficiently complementary to p53 RNA to reduce the production of p53 within the allograft organ via RNA-induced silencing complex (RISC), and wherein said vascular perfusion effectively delivers the RNAi agent to cells within the allograft organ so as to counter apoptosis-induced ischemic injury of the allograft organ, wherein the method is carried out in the absence of electroporation.

2. The method of claim 1, wherein the allograft organ is an allograft kidney or liver.

3. The method of claim 1, wherein perfusing the vasculature of the allograft organ with an RNAi agent capable of downmodulating ischemia-induced apoptosis further comprises administering the RNAi agent in a preservation solution that comprises either saline or an immunosuppressant.

4. The method of claim 1, wherein the RNAi agent is an siRNA molecule.

5. The method of claim 1, wherein the RNAi agent is an shRNA molecule.

6. The method of claim 1, wherein the RNAi agent comprises an oligonucleotide comprising a modification to a 2'-OH group, the modification being selected from the group consisting of the 2'-OH group replaced by a H, alkoxy or OR, halogen, SH, SR, amino, or CN group, wherein R is a lower alkyl, alkenyl, alkynyl, or aryl.

7. The method of claim 6, wherein the RNAi agent comprises a 2'-O-methyl oligonucleotide.

8. The method of claim 1, wherein the allograft organ is perfused with a solution containing said RNAi agent by retrograde or anterograde delivery.

9. The method of claim 1, wherein the perfused RNAi agent contacts the allograft organ via lipid-mediated delivery or as a component of a liposomal delivery preparation.

* * * * *